United States Patent
Butz-Ostendorf

(10) Patent No.: US 12,142,379 B2
(45) Date of Patent: Nov. 12, 2024

(54) COMPUTING A PATHOLOGICAL CONDITION

(71) Applicant: Labvantage-Biomax GmbH, Planegg (DE)

(72) Inventor: Markus Butz-Ostendorf, Landsberg am Lech (DE)

(73) Assignee: Labvantage—Biomax GmbH, Planegg (DE)

( * ) Notice: Subject to any disclaimer, the term of this patent is extended or adjusted under 35 U.S.C. 154(b) by 404 days.

(21) Appl. No.: 17/614,806

(22) PCT Filed: Jun. 3, 2019

(86) PCT No.: PCT/EP2019/064373
§ 371 (c)(1),
(2) Date: Nov. 29, 2021

(87) PCT Pub. No.: WO2020/244734
PCT Pub. Date: Dec. 10, 2020

(65) Prior Publication Data
US 2022/0230752 A1    Jul. 21, 2022

(51) Int. Cl.
*G16H 50/20* (2018.01)
*G06T 7/00* (2017.01)
(Continued)

(52) U.S. Cl.
CPC .......... *G16H 50/20* (2018.01); *G06T 7/0012* (2013.01); *G06V 10/426* (2022.01); *G16H 30/40* (2018.01);
(Continued)

(58) Field of Classification Search
CPC ...... G16H 50/20; G16H 30/40; G06V 10/426; G06T 7/0012; G06T 2207/20072; G06T 2207/30016
See application file for complete search history.

(56) References Cited

U.S. PATENT DOCUMENTS

2005/0245109 A1* 11/2005 Torres ................ H01R 13/6582
                                                        439/76.1
2018/0279940 A1* 10/2018 Campbell ................ A61B 5/70

FOREIGN PATENT DOCUMENTS

WO    WO-2018149930 A1 *  8/2018  ............. G16B 45/00

OTHER PUBLICATIONS

Sebastian J. Kopetzky et al: "From Matrices to Knowledge: Using Semantic Networks to Annotate the Connectome", Frontiers in Neuroanatomy, vol. 12, Dec. 7, 2018 (Dec. 7, 2018), XP055665332, DOI: 10.3389/fnana.2018.00111 (Year: 2018).*

(Continued)

*Primary Examiner* — John J Lee
(74) *Attorney, Agent, or Firm* — Occhiuti & Rohlicek LLP

(57) ABSTRACT

A computer-implemented method for computing a pathological condition of a subject, comprising obtaining (10) initial cranial image data of a subject from an input interface, and incorporating the initial cranial image data into a knowledge model comprised within a semantic network stored in a memory performing (12), via a processor, at least one processing sequence on the initial cranial image data using the semantic network to thus provide, in the semantic network, at least one element comprising topographical data of the subject's brain, or a portion of the subject's brain, referenced to a reference coordinate system wherein the at least one processing sequence performs at least one state iteration of at least a portion of the semantic network from a first state into a second state comparing (14) the topographical data of the subject's brain to one, or more pathological condition prediction elements of the semantic network to form an indication of a pathological condition of the subject, and generating (16) an additional element in the (Continued)

semantic network comprising the indication of the pathological condition of the subject.

18 Claims, 20 Drawing Sheets

(51) Int. Cl.
    *G06V 10/426*     (2022.01)
    *G16H 30/40*     (2018.01)

(52) U.S. Cl.
    CPC ............... *G06T 2207/20072* (2013.01); *G06T 2207/30016* (2013.01)

(56) References Cited

OTHER PUBLICATIONS

Losko, Sascha et al., Knowledge Networks of Biological and Medical Data: An Exhaustive and Flexible Solution to Model Life Science Domains, Data Integration in the Life Sciences pp. 232-239 (2006).

Cano, Isaac et al., "The COPD Knowledge Base: Enabling Data Analysis and Computational Simulation in Translational COPD Research," Journal of Translational Medicine, 12 (Suppl 2): S6 (9 pages) (2014).

Maier, Dieter et al., "Knowledge Management for Systems Biology A General and Visually Driven Framework Applied to Translational Medicine," BMC Systems Biology, 5:38, 16 pages (2011).

Maier, Dieter et al., "The BioXMTM Knowledge Management Environment: A General and Visually Driven Framework Applied to the Integration of Large Biological Datasets," 24 pages (2014).

Rinke, Sebastian et al., "A Scalable Algorithm for Simulating the Structural Plasticity of the Brain," J. Parallel. Distrib. Comput. 120 (2017): 16 pages.

Diaz-Pier, Sandra et al., "Automatic Generation of Connectivity for Large-Scale Neuronal Network Models through Structural Plasticity," Frontiers in Neuroanatomy, vol. 10, Article 57, 15 pages, (2016).

Baker, Justin T. et al. "Functional Connectomics of Affective and Psychotic Pathology," PNAS, vol. 116, No. 18, pp. 9050-9059 (2019).

Lee, Megan et al., "Resting State fMRI: A Review of Methods and Clinical Applications," AJNR Am J Neuroradiol. 34 (10): 1866-1872 (2013).

Taylor, Peter N. et al., "Within Brain Area Tractography Suggests Local Modularity Using High Resolution Connectomics," Scientific reports 7.1 (2017): 1-9.

Torgerson, Carinna M. et al., "DTI Tractography and White Matter Fiber Tract Characteristics in Euthymic Bipolar I Patients and Healthy Control Subjects," Brain Imaging Behav. 7(2): 129-139 (2013).

\* cited by examiner

COMPUTING A PATHOLOGICAL CONDITION

CROSS REFERENCE TO RELATED APPLICATIONS

This application is a National Stage of International Application No. PCT/EP2019/064373 filed on Jun. 3, 2019, the contents of which are hereby incorporated by reference in their entirety.

FIELD OF THE INVENTION

The present invention is in the field of bioinformatics, and aspects concern an apparatus for computing a pathological condition of a subject and an associated method, system, computer program element, computer readable medium, client-side device and server-side device.

BACKGROUND

Pathologies of the human brain are difficult to diagnose and to classify. Increasingly different brain disorders are not viewed as discrete diseases to be considered in isolation from each other. Instead, many different brain disorders are considered to be linked, presenting with similar symptoms. For example, the paper *"Functional connectomics of affective and psychotic pathology"* by Justin T Baker, et al (PNAS, 30 Apr. 2019, vol. 116, no. 18, pp. 9050-9059) argues that the presence of affective and psychotic illness is associated with graded disruptions in frontoparietal network connectivity, and that common features of the connectome are disrupted across distinct forms of pathology.

This revolutionary diagnostic framework is difficult to apply in medical practice because of the small differences that need to be tracked in the connectome of a patient. Significant research efforts have resulted in databases such as the Human Allen Brain Atlas and the Montreal Neurological Atlas (MNI). Furthermore, the Human Connectome Project (www.humanconnectomeproject.org) has made anonymized brain image data and connectome data available for researchers. The Brede ontology is a database containing data entries with an assessment of the functional behaviour of the human brain with relevant brain areas involved in a respective cognitive task. Many hospitals possess advanced brain imaging suites comprising MRI scanners CT scanners, PET scanners and MEG images.

The use of the ever-increasing amount of data available for a medical professional to make a neurological diagnosis is, in practice, hindered by the complexity of integrating data from many different sources. For example, integrating and enriching a patient MRI scan using research databases is still a challenging and time consuming task requiring image processing experts and computer programmers.

Some attempts have been made to integrate connectomic data with gene data. US 2019/0102511 A1 discusses tools and methods for analysing brain neuroimaging and gene expression maps to identify drug targets associated with neurobehavioural phenotypes and, conversely, neurobehavioural phenotypes associated with potential drug targets. However, to fully integrate new connectomics techniques into the diagnostic workflow in a busy hospital, for example, there is still a need to improve the integration of connectomic data and medical imaging data.

SUMMARY

According to a first aspect, there is provided an apparatus for computing a pathological condition of a subject. The apparatus comprises an input interface, a processor, a memory, and an output interface.

The input interface is configured to obtain initial cranial image data of a subject from the input interface, and to incorporate the initial cranial image data into a knowledge model comprised within a semantic network stored in the memory.

The processor is configured to perform at least one processing sequence on the initial cranial image data using the semantic network to thus provide, in the semantic network stored in the memory, at least one element comprising topographical data of the subject's brain, or a portion of the subject's brain, referenced to a reference coordinate system.

The processor is configured to perform the at least one processing sequence comprising at least one state iteration of at least a portion of the semantic network in the memory from a first state into a second state.

The processor is configured to compare the topographical data of the subject's brain to one, or more pathological condition prediction elements of the semantic network in the memory to form an indication of a pathological condition of the subject.

The processor is configured to generate an additional element in the semantic network comprising the indication of the pathological condition of the subject.

An effect is that a significant body of data may be automatically searched, and efficiently processed, using a computer to form an indication of the pathological condition of a subject. The application of a semantic network for generating the indication of the pathological condition of the subject implies that a large number of data sources can be structured using a formal linguistic specification defined by the data sources and other elements that are members of the semantic network. Whereas previously a "brute-force" search approach in a connectome search space defined by the initial cranial image data of the subject would have been required, the provision of a formal linguistic specification defined by elements of the semantic network enables focused and structured queries to be utilised to automatically and to efficiently search a large corpus of data.

Image processing and connectome processing workflows are referenced to a reference coordinate system of the semantic network according to aspects, and therefore the quality of image registration between the workflows is improved.

The processing of the data according to aspects requires significant computational effort. The use of a semantic network to act as an overarching monitor and to allocate and to coordinate processing of tasks between compute resources leads to improved scheduling and a reduce risk of hardware deadlocks occurring on processing servers.

The semantic network approach according to the first aspect is also highly adaptive. As new elements are added to the semantic network, or as elements are subtracted from the semantic network, the formal linguistic specification but may be used to search for data in the semantic network adapts. Accordingly, a lay user of the semantic network (such as a medical professional) can obtain powerful insights into the initial cranial image data loaded into the semantic network without needing to be able to provide a new computer code.

Previously, obtaining initial cranial image data of the subject has proved to be a difficult task requiring specialists in image processing and computer coding. Such specialists are usually not present in a busy hospital, and even in a university or research hospital, if present they are not integrated into the daily clinical process. However, the connectome-based diagnostic approach discussed in the specification requires the comparison and processing of initial cranial image data. Accordingly, the semantic network approach facilitates the loading of initial cranial image data into a semantic network and substantially automates, or at least simplifies the processing of the initial cranial image data. Accordingly, entirely new diagnostic opportunities are provided against neurological disease. In much the same way as a medical professional can quickly obtain the physiological status of a patient by performing an automatic blood test, the connectome-based diagnostic approach enabled by the semantic network discussed herein facilitates an automatic, or "more-automatic" (user-guided) neurological diagnosis approach.

In examples, the processor is further configured to generate a subject connectivity graph element of the least one topographical data in the semantic network, wherein the subject connectivity graph element comprises a subject connectivity graph representation of nodes and interconnections between nodes based on functional and/or structural connections between a portion of the subject's brain.

A technical effect is that the connectome is used as a biomarker for neurological disease. In particular, a connectome may be represented with a significantly smaller amount of data than, for example, a set of initial cranial image data. Therefore, when assessing the likelihood that a subject is suffering from a neurological disease, searching and/or comparing the connectome reduces the amount of computation required by several orders of magnitude, compared to a diagnosis technique applied on the initial cranial image data. Furthermore, a connectome may be represented in a smaller amount of memory than initial cranial image data. Storing, encrypting, and/or transmitting a connectome, or portion of a connectome over a network to a remotely located diagnostician, is more efficient than transmitting a full set of initial cranial image data.

In examples, the processor is configured to calculate a subject connectivity statistic of the nodes of the subject connectivity graph element; and to provide the indication of the pathological condition of the subject by comparing the subject connectivity statistic to a pathological condition prediction statistic.

A technical effect is that a connectome can be used as a biomarker for neurological disease.

In examples, the subject connectivity statistic is at least one of associativity, density, modularity, mean of the shortest paths, efficiency, transitivity, weighted characteristic path length, weighted clustering coefficient, small-world parameter, betweenness centrality, or local efficiency of the subject connectivity graph, or a portion of the subject connectivity graph.

A technical effect is that many different diseases can be characterised using a range of statistics, improving the sophistication and accuracy of a connectome-based diagnosis.

In examples, the processor is configured to obtain at least one template connectivity graph element representing a pathological condition, wherein the template connectivity graph element comprises an idealized, averaged, control, or measured template connectivity graph indicative of a brain, or portion of a brain wherein the template connectivity graph is indicative of a neurological condition, to compare, within the semantic network, portions of the template connectivity graph with corresponding portions of the subject connectivity graph representation, to identify similarities of the template connectivity graph and the corresponding portions of the subject connectivity graph representation; and to provide the indication of a pathological condition of the subject if the similarities of the template connectivity graph and the corresponding portions of the subject connectivity graph exceed a threshold.

A technical effect is that a computationally efficient comparison may be made between one, or more experimentally obtained connectomes that serve as a biomarker for neurological disease, and a connectome from initial cranial image data of a subject patient.

In examples, the subject connectivity statistic and/or template connectivity graph characterize Multiple Sclerosis or Alzheimer's disease.

A technical effect is that a rapid diagnosis of these diseases can be obtained by a medical professional without requiring the intervention of a skilled programmer or image processing professional, for example In examples, the processor is further configured to annotate the topographical data with a brain atlas defining brain regions registered to the topographical data in the reference coordinate system, to enlarge a formal grammar of the semantic network based on the brain regions defined in the brain atlas, and to generate the additional element in the semantic network comprising the indication of the pathological condition of the subject based on a selection of at least one brain region in the brain atlas.

A technical effect is that annotation of brain areas in the topographical data using a brain atlas the semantic network enables an efficient and accurate search of subsets of brain regions of interest that may also serve as biomarkers for neurological disease.

In examples, the processor is further configured to annotate the topographical data with a functional and/or anatomical ontology of brain structures defining functional and/or anatomical properties of brain regions registered to the topographical data in the reference coordinate system, to enlarge a formal grammar of the semantic network based on the functional and/or anatomical ontology of brain regions, and to generate the additional element in the semantic network comprising the indication of the pathological condition of the subject based on a selection of at least one brain structure in the functional and/or anatomical ontology.

A technical effect is that annotation of brain areas in the topographical data using a brain atlas the semantic network enables an efficient and accurate search of subsets of brain regions of interest that may also serve as biomarkers for neurological disease.

In examples, the input unit is configured to obtain symptom data input classification data of the subject from the input interface, wherein the processing unit is configured to incorporate the symptom data into the knowledge model comprised within a semantic network stored in a memory, and to form the indication of the pathological condition of the subject in the semantic network using the symptom data and the at least one element comprising topographical data.

A technical effect is that the accuracy of the diagnosis using connectomics techniques can be improved based on symptoms of a patient.

In examples, the processing unit is configured to select a subset of the topographical data of the subject's brain based on the symptom data, and optionally a brain atlas comprised in the semantic network, and to form the indication of the pathological condition of the subject based on the subset of the topographical data and/or the symptom data.

In examples, the initial cranial image data of the subject comprises a first time index defining an acquisition time of the initial cranial image data. The input interface is further configured to obtain subsequent cranial image data of the subject from the input interface at a second time index, and the processor is further configured to incorporate the subsequent cranial image data into the knowledge model comprised within the semantic network stored in the memory and to perform a further processing sequence on the initial cranial image data using the semantic network to thus provide, in the semantic network stored in the memory, a second element comprising topographical data at a second time index on the subsequent cranial image data using the semantic network to thus generate a further additional element in the semantic network comprising a further indication of the pathological condition of the subject at the second time index.

The processor is configured to compare the additional element and the further additional element in the semantic network to identify a change in the pathological condition in-between the first time index and the second time index.

A technical effect is that disease progression can be efficiently monitored by observing changes in a connectome. Because a connectome can be modelled using a graph, or vectors between nodes, the computational complexity of making a comparison between first and second connectomes obtained different times is significantly reduced, compared to comparing two three-dimensional sets of initial cranial image data of a subject observed at different times. Furthermore, the connectome is more closely related to brain function, implying that a diagnosis obtained by comparison of first and second connectomes is more accurate than a diagnosis of neurological symptoms performed on subsequently obtained three-dimensional sets of initial cranial image data.

In examples, the processor is further configured to access, via or in the semantic network, a neurological simulation element, wherein the neurological simulation element is configured obtain the at least one element comprising topographical data as a starting point of a neurological simulation, and to generate a simulated topographical data element in the semantic network as an output of the neurological simulation element applied to the topographical data.

A technical effect is that the potential evolution of a neurological condition may be more easily predicted. Furthermore, the effect on the connectome of the potential evolution of the neurological condition obtained by simulation may be used to interrogate the semantic network to predict further symptoms that a patient can expect to experience.

In examples, the processor is configured to store, in the memory, the initial cranial image data and the at least one element comprising a topographical data of the subject's brain, or a portion of the subject's brain, in a segregated subdivision of the semantic network.

A technical effect is one of improved security. The strong type control of elements of a semantic network is ideally suited to providing security privileges, or encrypting certain elements of a semantic network, to ensure that private patient data is safely held.

The processor is configured to perform subsequent processing of the initial cranial image data, or the topographical data, or data derived from them, exclusively within the segregated subdivision of the semantic network; and wherein any subsequent access to the initial cranial image data or the topographical data in the segregated subdivision of the semantic network by an unsegregated portion of the semantic network requires user authentication.

In examples, the input interface is configured to obtain user authentication data from the input interface.

The processor is configured to verify, based on the user authentication data, that the user has a security privilege allowing access to the segregated subdivision of the semantic network.

The processor is configured to process at least one of the subject connectivity graph element, the subject connectivity statistic, the additional element comprising the indication of the pathological condition of the subject and/or the indication of a pathological condition in the segregated subdivision of the semantic network; if the user has security privileges to access the segregated subdivision of the semantic network.

A technical effect is that user access to sensitive diagnostic information can be strictly controlled.

In examples, the processor is configured to encrypt the segregated subdivision of the semantic network, wherein decryption of the segregated subdivision of the semantic network requires user authentication.

A technical effect is that user access to sensitive diagnostic information can be strictly controlled.

In examples, the output interface is configured to output the indication of the pathological condition of the subject based on the additional element in the semantic network.

In examples, the input interface is configured to receive a user query.

The processor is configured to generate a request by transforming the user query into the formal linguistic specification defined by the semantic network.

The output interface is configured to obtain an output report to display the indication of the pathological condition of the subject using the additional element in the semantic network based on the user query.

In examples, the processor is configured to generate an output image illustrating the intrinsic functional connectivity of the topographical data of the subject's brain. The output interface is configured to display the output image to a user.

In examples, the processor is configured to generate output classification data of the subject based on the indication of a pathological condition in the additional element in the semantic network. The output interface is configured to output a report comprising the output classification data.

In examples, the initial cranial image data comprises structural MRI data, and the at least one processing sequence comprises a structural MRI data processing workflow.

In examples, the initial cranial image data comprises MRI data, and the at least one processing sequence comprises a functional MRI data processing workflow.

In examples, the initial cranial image data comprises PET (positron emission tomography) data, and the at least one processing sequence comprises a PET data processing workflow.

In examples, the initial cranial image data comprises DTI data, and the at least one processing sequence comprises a DTI data processing workflow.

In examples, the initial cranial image data comprises MEG data, and the at least one processing sequence comprises a MEG data processing workflow.

In examples, the semantic network is implemented as a relational database, or an object-oriented database stored in the memory.

In examples, the initial cranial image data comprises OCT image data (optical coherence tomography).

In examples, the initial cranial image data comprises SWI data (susceptibility weighted imaging).

In examples, the initial cranial image data comprises MRN (magnetic resonance neurography)

A technical effect is that a medical professional does not need to be able to compose database queries for a relational database or an object-oriented database, because the semantic network disguises the task of generating queries for the underlying databases.

Subsequent aspects will now be summarized. The reader will note that specific embodiments of the subsequent aspects are not repeated in the summary, but are provided in the dependent claims, and discussed in the detailed description.

According to a second aspect, there is provided a computer-implemented method for computing a pathological condition of a subject. The computer implemented method comprises:
 a) obtaining initial cranial image data of a subject from an input interface, and incorporating the initial cranial image data into a knowledge model comprised within a semantic network stored in a memory;
 b) performing, via a processor, at least one processing sequence on the initial cranial image data using the semantic network to thus provide, in the semantic network, at least one element comprising topographical data of the subject's brain, or a portion of the subject's brain, referenced to a reference coordinate system;
wherein the at least one processing sequence performs at least one state iteration of at least a portion of the semantic network from a first state into a second state;
 c) comparing the topographical data of the subject's brain to one, or more pathological condition prediction elements of the semantic network to form an indication of a pathological condition of the subject; and
 d) generating an additional element in the semantic network comprising the indication of the pathological condition of the subject.

According to a third aspect, there is provided a system for computing a neurological condition of a subject, comprising: a medical image acquisition apparatus and an apparatus according to the first aspect or its optional embodiments. The medical image acquisition apparatus is one or more of an MRI scanner, a CT scanner, a PET scanner, or a MEG scanner.

According to a fourth aspect, there is provided a computer program element comprising instructions which, when executed by a computer, enables the computer to carry out the computer-implemented method according to the second aspect, or its optional embodiments.

According to a fifth aspect, there is provided a computer program product, tangibly embodied on a carrier medium, comprising the program element of the fourth aspect.

According to a sixth aspect, there is provided a client-side device comprising:
 a client input interface, a client processor, a client memory, and a client output interface. The client input interface is configured to obtain initial cranial image data of a subject from the input interface and/or a user query, and a user authentication token. The client processor is configured to encrypt the initial cranial image data and/or the user query based on the user authentication token. The client output interface is configured to transmit the encrypted initial cranial image data and encrypted user query to a server-side device. The client input interface is configured to receive an encrypted output report from the server-side device. The processor is configured to decrypt the output report based on the user authentication token, and the client output interface is configured to display the output report to the user.

According to a seventh aspect, there is provided a server-side device; comprising a server input interface, a server processor, a server memory, and a server output interface.

The server input interface is configured to receive encrypted initial cranial image data and encrypted user query from a client side device. The server processor is configured to incorporate the initial cranial image data into a knowledge model comprised within a semantic network stored in the server memory. The server processor is configured to perform, via the server processor, at least one processing sequence on the initial cranial image data using the semantic network to thus provide, in the semantic network, at least one element comprising topographical data of the subject's brain, or a portion of the subject's brain, referenced to a reference coordinate system. The at least one processing sequence performs at least one state iteration of at least a portion of the semantic network from a first state into a second state.

The server processor is further configured to compare the topographical data of the subject's brain to one, or more pathological condition prediction elements of the semantic network to form an indication of a pathological condition of the subject. The server processor is further configured to generate an encrypted output report comprising the indication of the pathological condition of the subject. The server output interface is configured to transmit the output report comprising the indication of the pathological condition of the subject to a client-side device.

An effect of this is that a diagnostic tool can be provided that leaves a minimal-footprint with regard to software or data at the user's side. The service can run in a web-client without any need for downloading software or (reference) data sets and installing or adapting code to the user's IT environment, whilst enabling secure transfer of data between the client and the server, and vice-versa.

According to a seventh aspect, there is provided a method for diagnosing a subject with a pathological condition. The method comprises obtaining one or more sets of initial cranial image data of a subject using one or more items of medical image acquisition equipment; and
providing the initial cranial image data of a subject to an input interface of an apparatus according to the first aspect. The method further comprises receiving from the output interface of the apparatus according the first aspect a report comprising output classification data of the subject.

The techniques discussed herein provide clinical decision support. In examples, the techniques discussed herein provide clinical decision support for multiple sclerosis.

In this specification, "topographical data" is data that enables insight about brain structure, and/or brain function at different positions inside patient brain, to be observed. For example, the "topographical data" comprises information about the distribution of white matter tracts inside patient brain so that insights about the connection of one brain area to another brain area can be provided.

In this specification, "reference coordinate system" refers to a coordinate system that, for example, enables comparison of like brain structures between a patient and a brain atlas, or a patient and other control patient data. For example, a coordinate system of initial cranial image data may be referenced to the coordinate system of a brain atlas using a registration technique such as rigid registration or non-rigid registration. A skilled person will appreciate that many options exist for providing a reference coordinate system. For example, all coordinate systems of external data sources such as brain atlases, gene atlases, and the like may be transformed into the coordinate system of the initial cranial image data. Alternatively, a transform coordinate system may be generated into which all data (the initial cranial image data, external data, and the like) is transformed.

While brain images are usually examined by visual inspection, the aspects described herein offer an objective approach to diagnosing pathological conditions using brain images. Every feature contained in an image, such as the volume of a brain areas, the functional activation, glucose metabolism and structural and functional connectivity is considered to be topographical data that can be attributed to a particular location in the image data set. Topographical data is stored and represented by the semantic network model and describes all relevant biomarkers or surrogate markers of a disease measured by multimodal brain imaging.

BRIEF DESCRIPTION OF THE DRAWINGS

Other characteristics and advantages will be apparent from the accompanying drawings, which form a part of this disclosure. The drawings are intended to further explain the invention and to enable a person skilled in the art to practice it. However, the drawings are intended as non-limiting examples. Common reference numerals on different figures indicate like or similar features.

DETAILED DESCRIPTION

Introduction

Figure 1:
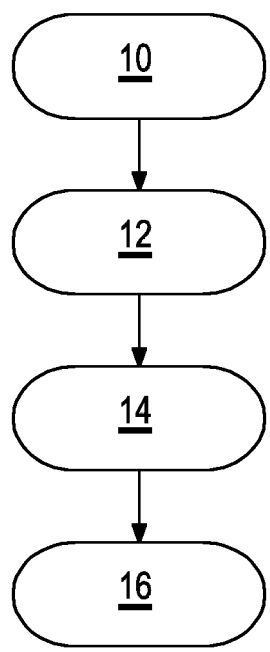
FIG. 1 illustrates a method according to an aspect.
Figure 2:
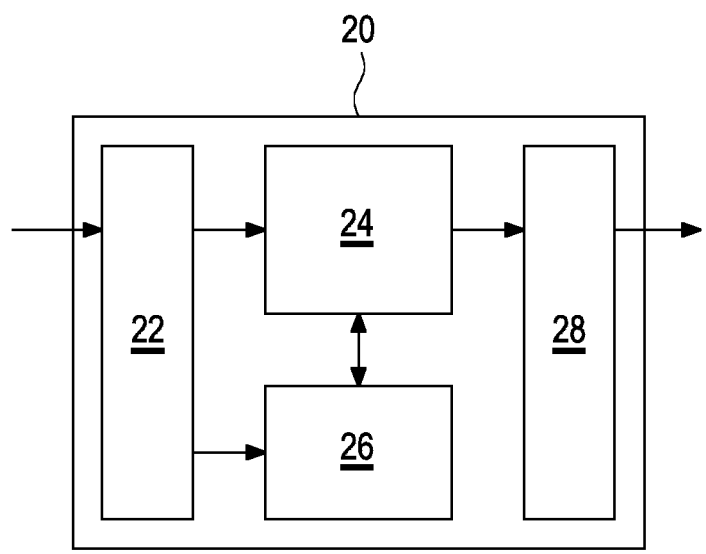
FIG. 2 illustrates an apparatus according to an aspect.

The present specification is concerned with neurological conditions that are caused by primary damage or degeneration of brain tissue and reactive functional reorganization of the connectome. For simplicity, the present specification will mainly consider multiple sclerosis as a neurological condition caused by primary or progressive brain damage or functional reorganisation of the connectome, although the reader will appreciate the techniques outlined herein have brought applicability to many other functional disorders.

In Multiple Sclerosis (MS), brain lesions form having areas with neural demyelination. The response of brain is to functionally reorganise connections affected by the brain lesion. The functional reorganisation can help the affected brain maintain and even restore to cognitive functions, but such a reorganisation may be disastrous if a degree of connectome rewiring is so significant that a catastrophic failure of brain networks is caused. An example of such a catastrophic failure may be observable in the transition from the diagnosis of the patient as being in a state of MS relapse remission, to entering the secondary progressive form of multiple sclerosis.

One MS classification comprises the set: "control" (HC), "clinical isolated syndrome (CIS)", "relapse remitting (RR)", "secondary progressive (SP)", and "primary progressive" (PP).

MS is typically diagnosed with observed symptoms, combined at a later stage with medical imaging and laboratory tests. Table 1 illustrates typical MS symptoms.

TABLE 1

| Symptoms of Multiple Sclerosis |
|---|
| Central |
| Fatigue |
| Cognitive impairment |
| Depression |
| Anxiety |
| Unstable mood |
| Urinary |
| Incontinence |
| Retention |
| Visual |
| Nystagmus |
| Optic neuritis |
| Diplopia |

TABLE 1-continued

Symptoms of Multiple Sclerosis

Bowel

Incontinence
Diarrhoea
Constipation
Throat

Dysphagia
Muscoskeletal

Weakness
Spasms
Ataxia
Speech

Dysarthria
Sensation

Pain
Hypoesthesia
Paraesthesia

MS is difficult to diagnose because so many of its symptoms are similar to, or overlap with, those of other pathologies (either neurological pathologies, or more general ones). Presently the McDonald criteria are the preferred form of diagnosis. The McDonald criteria use a combination of clinical and laboratory tests at different times, dependent on how many attacks and lesions are present. However the McDonald criteria lack specificity, and it is recommended that the presence of many other diseases is ruled out before applying the McDonald criteria.

In short, diagnosing MS is a challenge even for experienced neurologists. Currently, no test short of a tissue biopsy is 100% specific for securing an MS diagnosis. MS therefore remains a clinical diagnosis supported by MRI and evoked potential studies. The diagnosis of MS is further complicated by the large number of conditions that can mimic the features of MS, such as Lyme disease and lupus erythematosus, resulting in misdiagnosis, and a missed opportunity for providing optimal therapy. According to the McDonald criteria, approximately 90% of MS patients are diagnosed on the basis of an MRI scan.

The publication "*Graph Theory-based brain connectivity for automatic classification of Multiple Sclerosis clinical courses*" (frontiers in neuroscience, 25 Oct. 2016, volume 10, article 478, doi: 10.3389/fnins.2016.00478 by Kocevar et. al) discusses one technique enabling automatic staging of Multiple Sclerosis using simple DTI images subjected to a structural brain connectivity analysis. The publication "*Intra-cortical conductivity in Multiple Sclerosis: a neurophysiological approach*" (Brain (2008), 131, 1783-1792, doi:10.1093/brain/awn087 by Tecchio et al) likewise proposes the use of an "intra-cortical connectivity index" focused on the primary somatosensory cortical areas.

In a busy clinical environment, an increasing emphasis is being placed on rapid and accurate diagnostic testing. Every-day clinical diagnosis has, however, arguably, not benefited from the potential of such new medical imaging and bioinformatics technologies. One reason for this may be that the integration of many disparate data sources necessary to perform automated connectome analysis in the case of functional neurological problems requires significant customization dependent on the patient, the medical scanners used to image the patient, and the like.

The present specification demonstrates a solution to rapid diagnostic testing for MS patients based on improvements in medical imaging and research in the field of functional brain reorganisation. In particular, an apparatus is provided that is able to generate detailed reports and medical images providing information about a diseased brain from medical imaging data automatically.

The solution comprises the steps required to enable a user to securely submit a patient's medical image data set to the apparatus, enable the automatic performance of pre-processing of the medical image data set, automated processing of relevant image features, the querying of matching healthy controls from integrated public databases, a comparison of individual patients to selected controls, and a generation of output reports as well as returning output reports to a user securely. Although the present specification discusses the application of such an apparatus to MS in detail, it will be appreciated that without lack of generality, the apparatus can be applied to provide results for any patient presenting with a functional brain disease undergoing neuro-radiological assessment.

The apparatus discussed herein automatically, or semi-automatically (in other words, optionally in a user-guided way) uses the BioXM™ Platform Technology (database) to provide more effective and timely brain imaging of MS patients. In particular, a subset of the BioXM™ Platform Technology referred to as the "NeuroXM™ suite" with customized features and links to external databases that are suitable for neurological patient investigations. In a clinical context, a patient may present with a range of symptoms as outlined in Table 1 above and may be given an initial medical scan using, for example, an MRI scanner. It would be advantageous to provide a diagnosis or an indication of a neurological condition using these inputs in a timely manner (for example on the same day as a patient imaging scan), rather than having to use the time-consuming staging approach discussed above. The conventional staging approach requires several weeks or months to discount diseases other than MS from the diagnosis. However, the application of the BioXM™ database is not essential, and other generic semantic network approaches could be used.

The BioXM™ Platform Technology

The applicant has discussed a data processing platform that may be customised for neurological data processing in WO 2018/149930 A1, which is hereby incorporated by reference. WO 2018/149930 A1 discusses the BioXM™ database implemented as a semantic network system provided by Biomax Informatics AG of Planegg, Germany. A semantic network is implemented using a database organised according to an ontology, where the ontology is defined at least according to the properties of the elements that are members of the semantic network, and the relations between the elements. This knowledge management tool is intended to provide a solution to the increasing amount of data present in the life-sciences field. WO 2018/149930 A1 proposes to order neuro-biological information based on the idea of connectomics. Furthermore, the annotation of connectomics information with other sources of information is enabled.

In WO 2018/149930 A1, it is explained that a typed data relationship between semantic data objects representing different "elements of a scientific domain" can be provided to a distinct neural relationship in a neurological image of the patient. For example, a link between at least two brain areas in absolute 3D space (or alternatively between parcellated brain areas) can be associated with a multitude of other data sources by annotating the link with further object information. For example, a link between two locations in the frontoparietal area may be annotated with a given entry in the Brede functional ontology, for example.

The BioXM™ database integrates objects from public and proprietary databases into a knowledge model implemented in a semantic network operating on an advanced relational database management system so that the integrated objects can serve as "virtual semantic objects". Semantic objects such as "elements", "relations", "contexts", "ontology instances", or "external database entries" can be annotated with additional information.

Because the objects are semantically linked inside knowledge model, a query language that may be used to query information inside the knowledge model is constantly adapted as new elements are added to the semantic network, and as existing elements in the semantic network change or evolve. The knowledge model can be viewed as a semantic network capable of being queried using a formal linguistic specification, wherein the formal linguistic specification is derived from the semantic network.

In technical terms, as each element is added to or subtracted from the semantic network, the set of possible queries that may be asked of the knowledge model grows or shrinks. The queries are, in practice, translated into a set of queries in database code (such as SQL). A representative query that may be entered into a knowledge model comprising (i) a brain atlas, (ii) experimental MRI data of the patient, and (iii) gene information from the Human Allen Brain Atlas is (verbatim):

"find all elements "brain structure" that are connected by a connection strength (correlation value) larger than 0.7 to an element "brain structure" that is related to experimental data "gene expression" that express a "gene" which in codes for an element "neural receptor protein" which has a name "fkbp5""

It can be appreciated that such a knowledge model operating on semantic principles can disguise the inherent complexity when interacting with complicated datasets composed of many sub-databases, each of which may have a size in the range of Gigabytes to Terabytes. The generation of complex SQL queries that may typically be tens or hundreds of pages long is achieved automatically, directly from the free-text query. The generated SQL code is applied to the underlying relational database that links constituents of the knowledge model. The result of a query can then be returned to a user.

For the sake of illustration, if the user suddenly removed the "Human Allen Brain Atlas" from the simple knowledge model discussed above, the query grammar "that is related to experimental data "gene expression" that express a "gene" which in codes for an element "neural receptor protein" which has a name "fkbp5 five"" would correspondingly not be available to the user of the knowledge model, because the element "Human Allen Brain Atlas" enabling the query grammar would not then be a part of the knowledge model of the semantic network.

Aspects

The invention will be explained and embodied with reference to the method steps of the second aspect. However, a skilled person will appreciate that the following explanation applies also to the other aspects presented in the summary section.

FIG. 1 illustrates a method according to the second aspect.

According to the second aspect, computer-implemented method for computing a pathological condition of a subject, comprising:

a) obtaining 10 initial cranial image data of a subject from an input interface 22, and incorporating the initial cranial image data into a knowledge model comprised within a semantic network stored in a memory;

b) performing 12, via a processor 24, at least one processing sequence on the initial cranial image data using the semantic network to thus provide, in the semantic network, at least one element comprising topographical data of the subject's brain, or a portion of the subject's brain, referenced to a reference coordinate system;
  wherein the at least one processing sequence performs at least one state iteration of at least a portion of the semantic network from a first state into a second state;

c) comparing 14 the topographical data of the subject's brain to one, or more pathological condition prediction elements of the semantic network to form an indication of a pathological condition of the subject; and d) generating 16 an additional element in the semantic network comprising the indication of the pathological condition of the subject.

In examples, the semantic network is implemented as a relational database, or an object-oriented database.

In exemplary implementations, the method is performed by a computing apparatus 20 such as a personal computer, or a server.

The input interface 22 obtains initial cranial image data of the subject via an input interface 22 that is connected to a data communications network. For example, the input interface 22 may communicate with the picture archiving and communication system (PACS) of a hospital via an ethernet connection. The input interface 22 can also comprise a tape drive, an interface to a portable hard drive, a USB interface, and the like. In examples, the input interface 22 is directly connected to a medical scanner such as an MRI scanner, a CT scanner, a PET scanner, or a MEG scanner, for example.

Functional magnetic resonance imaging (fMRI) uses a MR scanner to detect changes in blood flow in a patient's brain. A fMRI scan may be taken in the resting state (RS-MRI) or with some level of functional activation. Highly oxygenated haemoglobin responds differently to a strong magnetic field as opposed to weekly oxygenated haemoglobin. This enables levels of brain activity to be inferred from an fMRI image.

Diffusion tensor imaging (DTI) examines the diffusion of water in tissue to identify the likelihood of a certain portion of tissue containing annual tract. It is assumed that water is more likely to align in the direction of the neural fibre bundle. Therefore, DTI enables anatomical connections between various brain areas to be obtained and visualised non-invasively. DTI is an imaging modality used to assemble the images in the "Human Connectome Project" (HCP). DTI enables the visualisation of white matter tracts in a brain.

Magnetoencephalography (MEG) is a functional neuroimaging technique. Magnetometers are placed around the brain of a subject, to enable the magnetic response of the brain to be measured response quickly and time to functional stimuli (on the order of milliseconds), as opposed to fMRI which is dependent on changes in blood flow. Therefore, MEG imaging is beneficial for accurately identifying changes in the auditory and sense areas of the patient.

Positron emission tomography (PET) involves imaging a patient shortly after they have ingested a substance comprising a radio ligand which is metabolised within the patient's body. As the patient is scanned in the PET scanner, the radio ligand emits positrons which can be detected by the PET scanner. The emission of the positrons is proportional to the metabolic rate in a given area of the patient. PET imaging is appropriate for discovering certain metabolic linked diseases.

All of the above imaging modalities provide initial image data that must be processed by a number of image processing pipelines before the connectome can be viewed. Of course, no individual combination of modalities is essential. Furthermore, medical imaging modalities not listed may be incorporated into the semantic network.

The paper "*The minimal preprocessing pipelines for the human connectome project*" (Glasser et. Al, NeuroImage 80 (2013) 105-124, Elsevier), comprehensively discusses one implementation of the minimal image processing pipelines required to take raw MRI data in the "CIFTI" format and to generate cortical surfaces, segmentation, and myelin maps, for example.

For example, in the case of fMRI, an original image in the "NIFTI" format is obtained as known to a person skilled in the art comprising T1w(s) and T2w(s) images and a registered field map. At a minimum, gradient distortion correction, alignment and averaging, read out distortion correction, and cross-modal registration between the T1w(s) and T2w(s) images should be performed.

After such pre-processing, there may be a step of taking the bias-corrected image, down-sampling it, and to perform a number of image processing steps to generate pial surfaces in the patient image. This step may, in examples, be performed by a tool such as "FreeSurfer", or another customised image processing pipeline.

Following generation of the pial surfaces, there may be a step of generating a final brain mask, and myelin maps.

The minimal processing pipelines implemented by the human can project are effective but intended for a research context. Applying these pipelines to newly captured MRI data in a clinical context is difficult, because computer programming and image processing experts are not typically available in a hospital.

According to aspects, a portion, or the entirety, of an image-processing pipeline is performed inside a semantic network, and in examples is implemented using the BioXM™ database.

Therefore, as an option of the method according to the second aspect, the T1w(s) and T2w(s) images and a registered field map from a fMRI scan are provided as the initial cranial image data of a subject. The initial cranial image data of the subject is loaded into a knowledge model comprised within a semantic network.

For example, in step a) of the method the initial cranial image data of the subject is loaded into an instance of the BioXM™ database executing on a computer or server. The initial cranial image data is, in examples, obtained in the "NIFTI" or "CIFTI" format, or in a third-party format from a MRI imaging apparatus manufacturer.

Step b) of the method according to the first aspect defines the automated pre-processing of the initial cranial image data using a semantic network, for example the BioXM™ database, to obtain topographical data of the subject brain.

As explained in WO 2018/149930 A1, elements in an instance of a BioXM™ database may be run-time extensible and processed within the knowledge model using scripting languages or code. Accordingly, the BioXM™ database provides an ideal platform for the automation of medical image processing pipelines.

Figure 3:
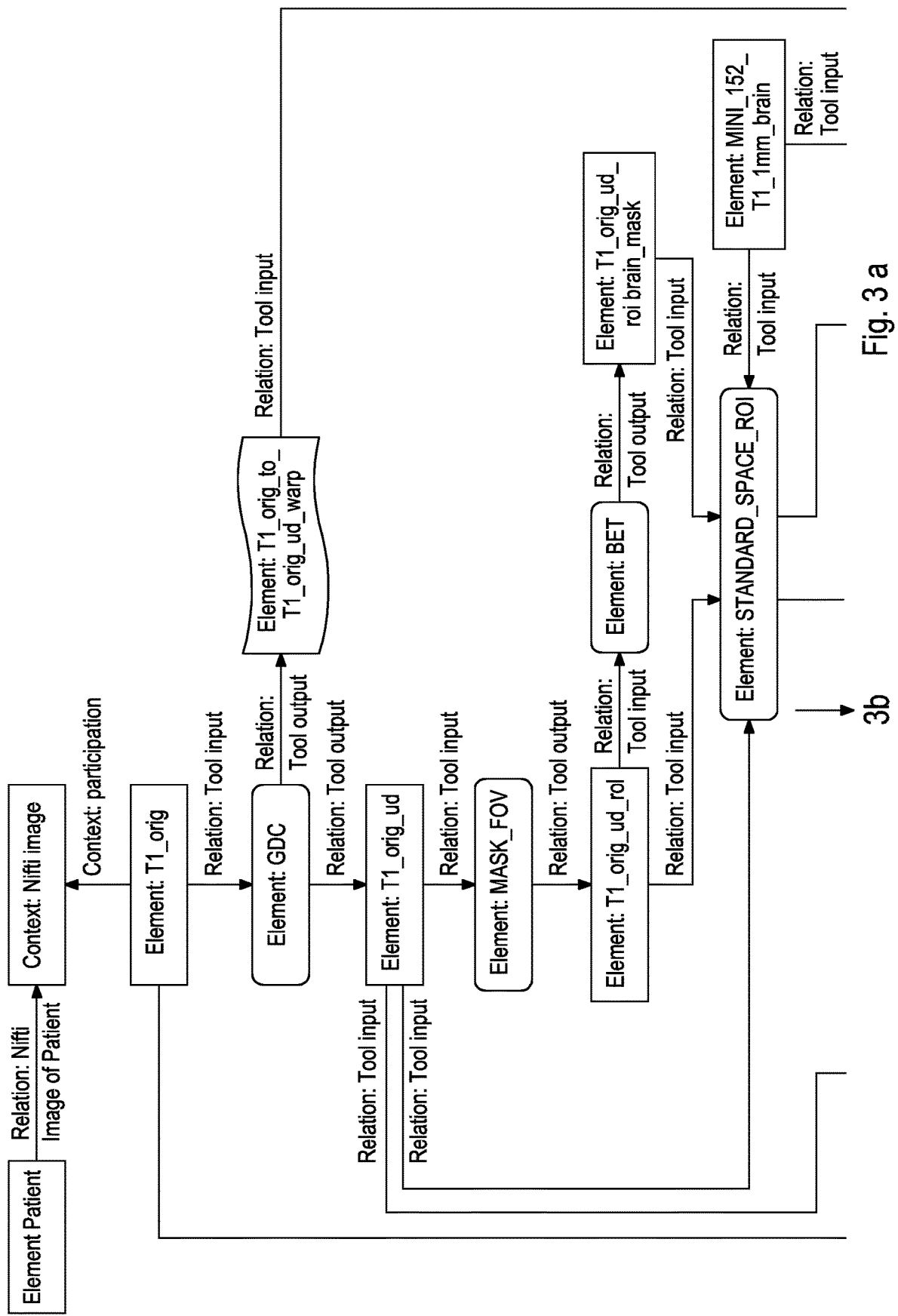
FIGS. 3a, 3b, and 3c schematically illustrate an input image processing pipeline implemented inside a semantic network.
Figure 3:
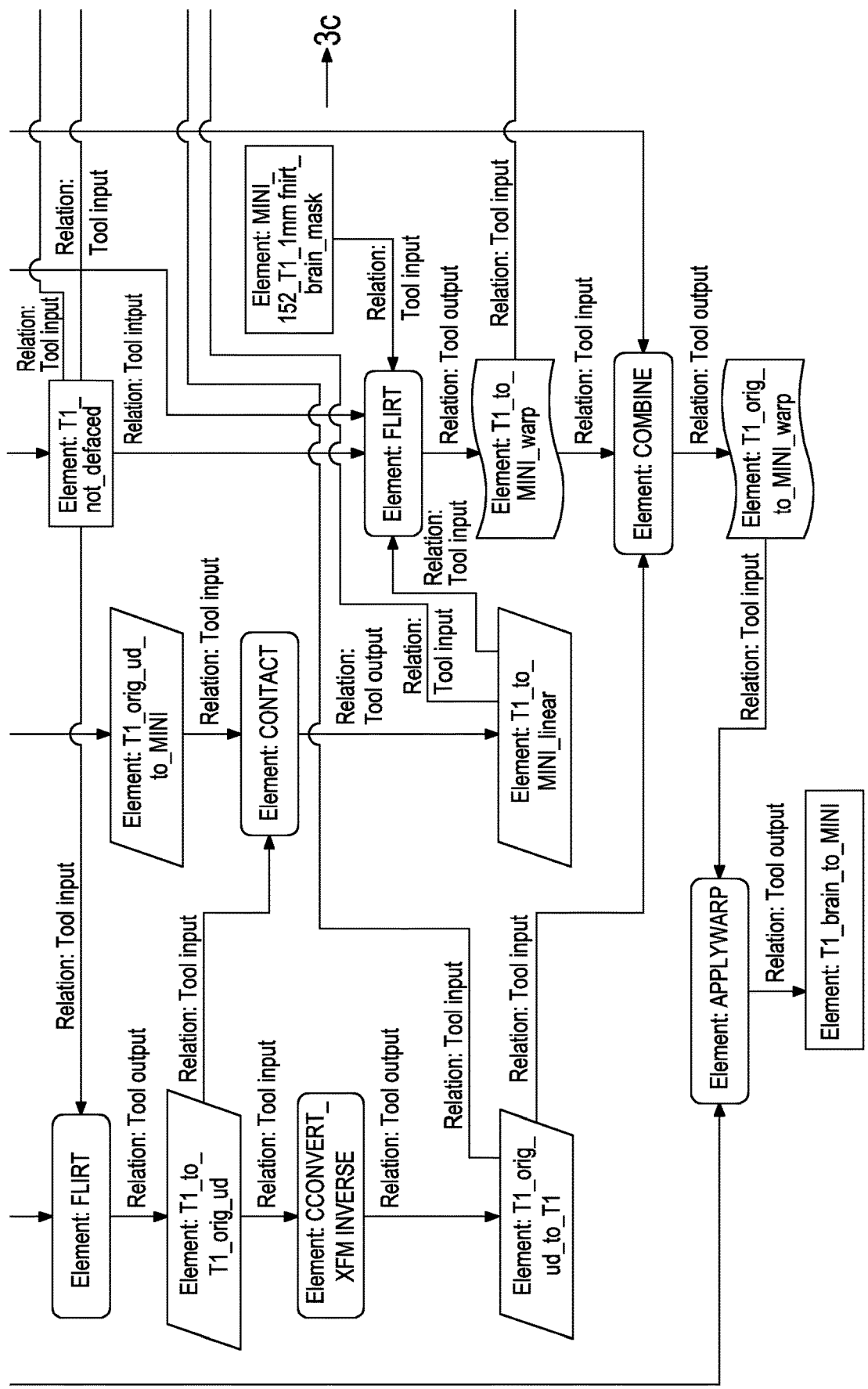
Figure 3:
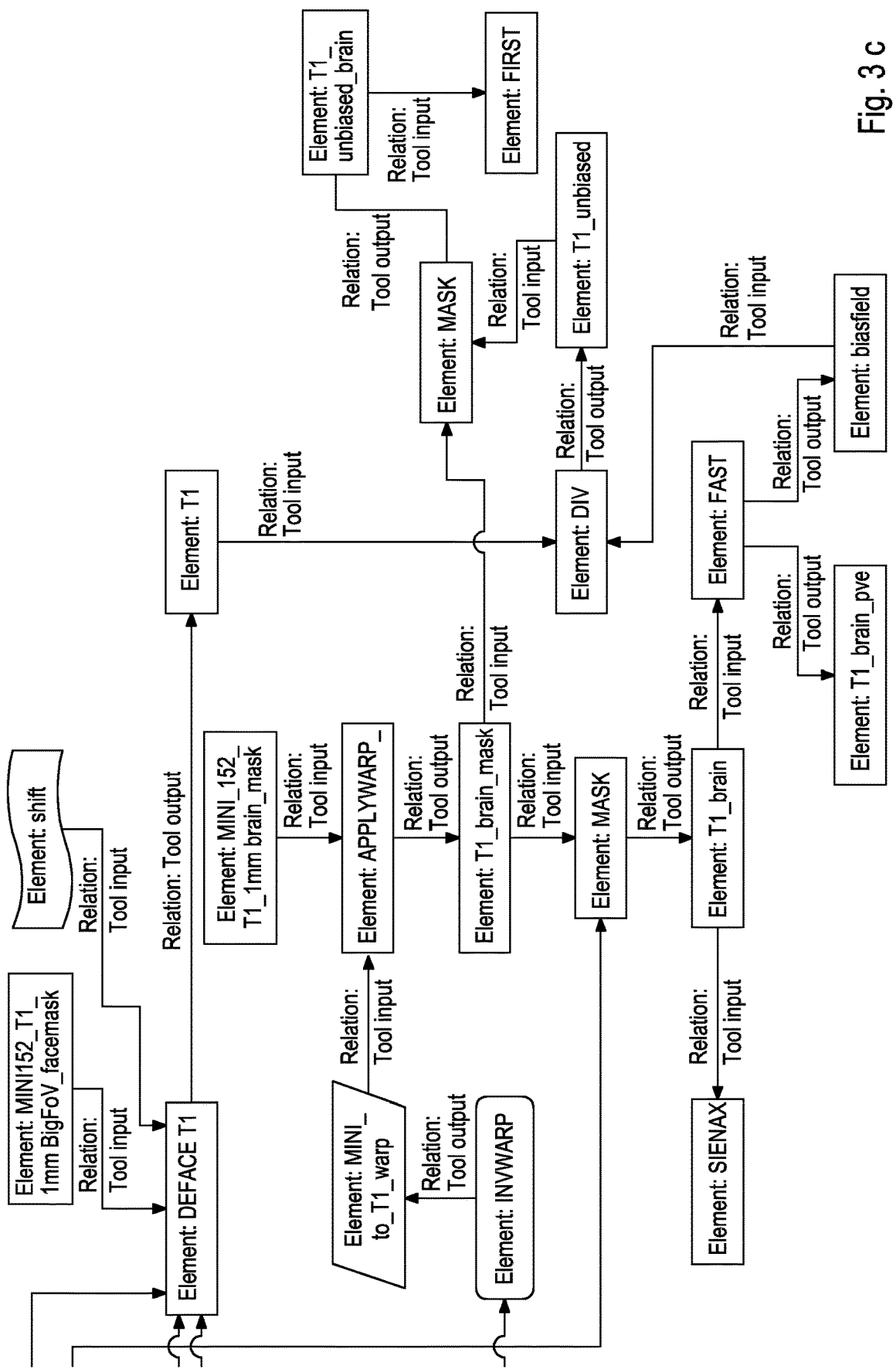

FIGS. 3a, 3b, and 3c illustrate a set of elements implemented within an instance of the BioXM™ database that provide one example of an initial image processing pipeline for fMRI data. In particular, FIGS. 3a, 3b, and 3c depict a typical preprocessing and processing pipeline of a structural T1-weighted MR image as published by Taylor et al., 2017.

In brief, the initial image processing pipeline for fMRI data takes an acquired fMRI image of an entire patient head, extracts the brain, segments the brain volume in grey and white matter and liquid, and then registers the image to a standard image space. The latter is necessary to be able to apply atlas information to parcellate the brain in disjunct areas and structures. Performing the process illustrated in FIGS. 3a, 3b, and 3c in the semantic network provides at least one element comprising topographical data of the subject's brain, or a portion of the patient's brain, referenced to a reference coordinate system.

Each "element" shown in FIGS. 3a, 3b, and 3c may perform a portion of the initial image processing pipeline and represents the progressive application of processing modules defined using, for example, a scripting language to intermediate portions of intermediate image data.

Advantageously, the execution of the image processing pipeline within the BioXM™ database means that many parameters that would previously have had to be tuned using the intervention of a skilled image processing operator can, instead, be provided automatically, or with less user intervention. Furthermore, because the pipeline is compartmentalised inside the BioXM™ database, overarching control over the coordinate system of the processing pipeline can be maintained between steps, thus improving registration of the images at various stages of the pipeline. The improved registration of the images at various stages of the pipeline improves imaging quality, and thus the quality of the derived connectome graphs.

Each step or sub-step of the image processing pipeline can be regarded as causing a small reconfiguration, or iteration, of the semantic network. Therefore, the process of providing the at least one element comprising topographical data of the subject brain, or a portion of the subject brain, can be viewed as a plurality of iterations of the state of the semantic network.

As one example of iterating the semantic network from a first state to a second state, an original NIFTI set of T1w(s) and T2w(s) images and a registered field map are comprised within the semantic network. However, each progression through the graph elements of FIGS. 3a, 3b, and 3c is an example of an iteration of the state of the semantic network. For example, the application of gradient distortion correction is typically performed by modelling the magnetic field generated by each gradient coil using spherical harmonic expansion. Then, a vector field representing the spatial distortion of the T1w(s) and T2w(s) images field is typically generated using a proprietary gradient coefficient file from a specific scanner used to acquire the T1w(s) and T2w(s) images. It will be appreciated that the application of gradient distortion correction is a succession of image processing operations that may be implemented using third-party MATLAB™ tools or other customised code. The process of converting the original NIFTI T1w(s) and T2w(s) images to gradient distortion corrected T1w(s) and T2w(s) is another example of one state iteration that is performed when converting the initial cranial image data into topographical data using the semantic network.

A further advantage of providing the image processing pipeline inside the semantic network is that third-party processing tools or image processing APIs (Application Processing Interfaces) can be flexibly integrated into the semantic network.

In examples, the plurality of iterations of the state of the semantic network are automatic. In examples, one or more of the iterations is user-guided via a graphical user interface.

The pre-configured pre-processing workflows enables an improvement in imaging quality. The knowledge model may comprise customised processing workflows for one or more of structural MRI, DTI, fMRI, and rs-fMRI. Third-party tools and customised MATLAB™ and/or Python™ scripts can be incorporated in, or linked to and from, the BioXM™ database. Automated quality control, and integration of data from third party databases is also facilitated.

The semantic network also improves the coherence of handling very large datasets. One set of gradient images used to generate topographical image data can have occupy around 200 Gb of memory. The implementation of an image processing pipeline for processing such images becomes a challenge in terms of how to schedule image processing pipeline stages on computing hardware. By implementing the image processing pipeline within a semantic network, fine control over execution of the various stages of the pipeline can be influenced in real time. In examples, the semantic network may interface with a "Hadoop" ™ controlled computational cluster for processing the initial cranial image data.

A significant advantage of implementing the image processing pipeline inside a semantic network is that very fine control over the full image processing pipeline can be automatically applied.

Furthermore, in a case where the method according to the first aspect is implemented in a server farm of a hospital, updates to the image processing pipeline (to reflect recent research improvements or "bug fixes", for example) can be provided and fine-tuned by third-party contractors, in examples, from remote locations.

It will therefore be appreciated that an output of step b) of the method according to the second aspect is topographical data of a subject brain. In examples, the output of step b) is data representing the connectivity of at least one brain location to another brain location. In examples, the output of step b) is a data representation of a connectome of a subject brain.

Although the example of providing a rs-fMRI image processing workflow within a semantic network has been discussed, the approach may be provided analogously in respect of other medical imaging modalities.

Figure 4:
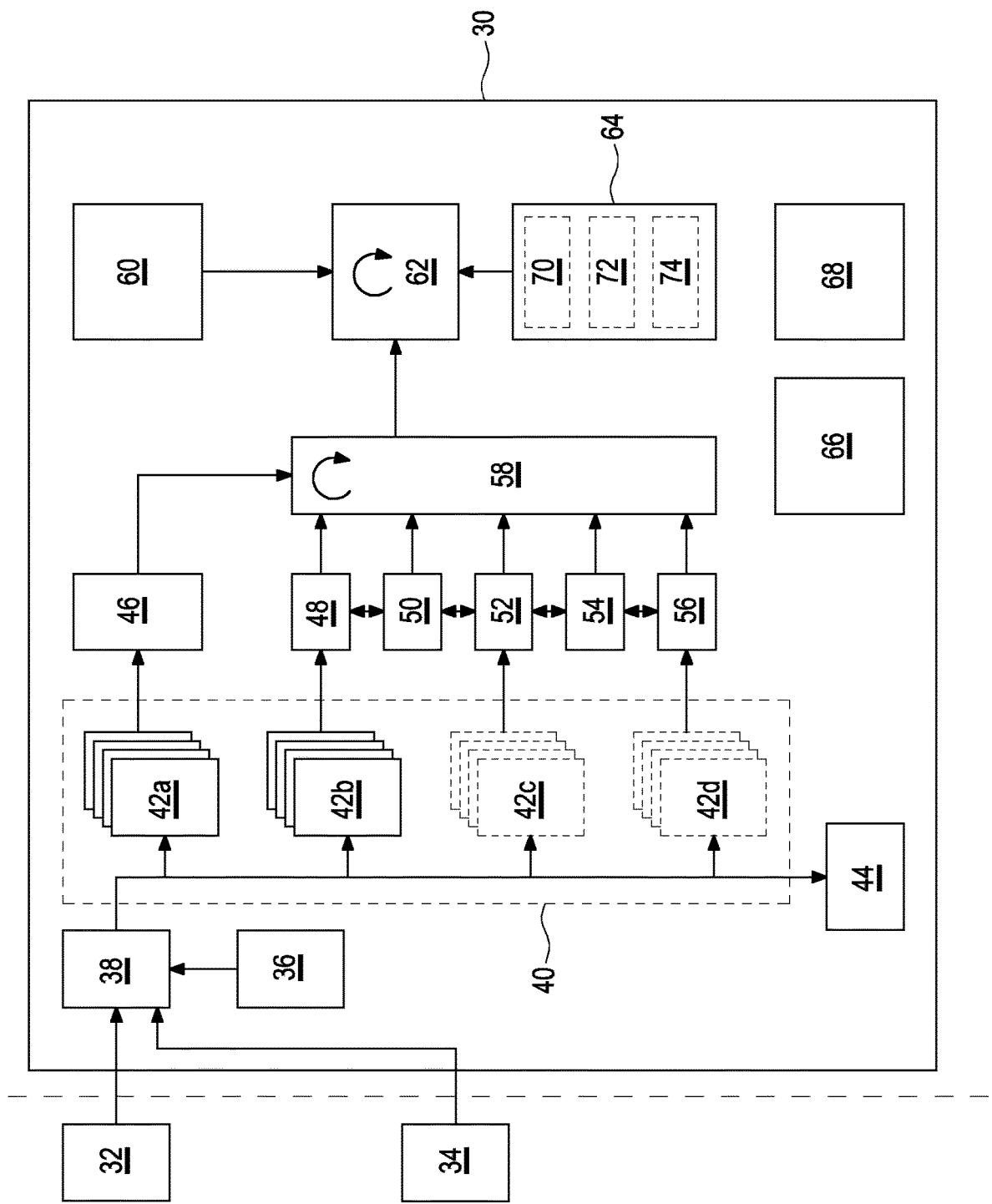
FIG. 4 schematically illustrates a workflow for connectomics diagnosis implemented using a semantic network.

FIG. 4 schematically illustrates a process for connectomics diagnosis implemented using a sematic network 30.

An input data source 32 is a medical scanner, such as an MRI scanner, a CT scanner, a MEG scanner, or a PET scanner, or any combination of these. Alternatively, the input data source 32 may be a server or other data source for providing previously obtained initial cranial image data of the subject. The data source 32 is configured to provide initial cranial image data of the subject to a semantic network via a data communications connection or network.

In examples, input databases 34 also input data into the semantic network. For example, the input is the publicly available "Human Allen Brain Atlas" or the publicly available "Human Connectome Project". The databases may be obtained directly, via an Internet connection, or via periodically archived copies stored locally to the computing device that the semantic network is operating on. For example, research results from such public databases can be used to enrich topographical data, or may be used to assist diagnosis. Owing to the advanced input data parsing capabilities of the BioXM™ database, the public databases appear to the semantic network to be elements directly incorporated into the semantic network. For example, if a brain atlas is linked to the semantic network, the fields of the brain atlas become incorporated into the ontology of the semantic network. Linking a brain atlas to the semantic network means that other elements in the semantic network may be searched according to entries in the brain atlas.

A patient data source 36 held and/or input into the semantic network 30 provides patient meta-data such as age, sex, a patient history (which may, in examples, be organised according to one or more of the various medical reporting ontologies).

A preprocessing stage 38 obtains the initial cranial image data of subject and removes (and stores), for example, manufacturer-specific headers and of the meta-data.

A set of input imaging workflows 40 automatically provides input imaging workflows 42a, 42b, 42c, 42d that are customised to the type of medical image available to the semantic network. In this example, input imaging workflow 42a is a structural MRI processing workflow. Input imaging workflow 42b is a functional MRI processing workflow. Input imaging workflow 42c is a DTI (diffusion tensor imaging) imaging workflow. Input imaging workflow 42d is a PET image processing workflow. The set of input imaging workflows 40 is not limited to those described here, and substantially any image processing or signal processing workflow relevant to diagnosis of a neurological pathology may be incorporated into the set of input imaging workflows 40.

The structural MRI processing workflow 42a and the functional MRI processing workflow 42b are illustrated in bold because these workflows are the most commonly used. The connectivity diagnosis functionality to be discussed subsequently may be provided with one or both of these input imaging workflows. However, the connectivity diagnosis functionality may be enriched with the results from further imaging modalities. The initial patient imaging data does not need to obtained contemporaneously to the execution of the workflows in the semantic network 30. In examples, archived or stored initial patient imaging data may be uploaded to the semantic network 30.

The input imaging workflows 42a, 42b, 42c, 42d are configured to process initial patient imaging data, and/or image data sets obtained from public databases 34. Input imaging workflows 42a, 42b, 42c, 42d may be executed in the semantic network serially, or in parallel. The semantic network may control allocation of the input imaging workflows 42a, 42b, 42c, 42d to different processes or servers.

The semantic network may control allocation of the input imaging workflows to different hardware elements based on a security level assigned to the input data. For example, input data that is publicly and freely available from anonymized research databases may be processed with a lower level of security, whereas the initial cranial image data of a subject must be processed with a higher level of security to reduce the risk that sensitive patient data becomes accessible to third parties.

FIGS. 3a, 3b, and 3c illustrate a set of elements implemented within an instance of the semantic network that provide one example of an initial image processing pipeline for fMRI data. In other words, element 42b of the semantic network 30 is, in one example, implemented according to the scheme of FIGS. 3a, 3b, and 3c. However, many additions and alterations to the fMRI image processing pipeline illustrated in FIGS. 3a, 3b, and 3c can be introduced without loss of generality to the wider semantic network 30.

The input imaging workflows 42a, 42b, 42c, 42d may, in examples, make functional calls to external processes 44, the API interfaces of proprietary programs, or to interfaces of public-domain programs. For example, external processes 44 can comprise one or more of MATLAB™ script or API, Python™ script, FreeSurfer™, or the like.

The output of one or more of the structural MRI input imaging workflow 42a, the functional MRI input imaging workflow 42b, the DTI input imaging workflow 42c, and/or the PET input imaging workflow 42d may be considered to be topographical data of the subject brain, or a portion of the subject brain, referenced to a reference coordinate system.

The output of the structural MRI input imaging workflow 42a may be input into a brain statistics module 46. The brain statistics module 46 computes one or more of brain volume, grey matter volume, white matter volume, cortical thicknesses, and the like. In examples, the semantic network 30 may feed-back the one or more brain statistics calculated in the brain statistics module 46 to one or more of the input imaging workflows 42a, 42b, 42c, 42d. High-level statistics obtained using a structural MRI input imaging workflow 42a can be used to inform or to alter the execution of one or more of the remaining input imaging workflows 42b, 42c, 42d. Furthermore, the statistics calculated in the brain statistics module 46 can be made available to the entire semantic network 30 to be used, for example, for results normalisation.

In examples, the output of the functional MRI input imaging workflow 42b is input into a functional brain area activation module 48. The functional brain area activation module 48 is configured to assess the functional activation of a portion of a subject brain. The functional brain area activation data is referenced to the reference coordinate system of the semantic network.

In examples, the output of the functional brain area activation module 48 is provided to a functional connectivity matrix generator 50. The functional connectivity matrix generator 50 calculates, for a first plurality of nodes of a subject brain, or portion of the subject brain, the strengths of the functional connections between a second plurality of nodes of the subject brain. The functional connectivity matrix generated by the functional connectivity matrix generator 50 is referenced to the reference coordinate system of the semantic network.

In examples, the DTI processing workflow 42c is configured to provide structural connectivity data to a fractional anisotropy computation module 52. Fractional anisotropy is a measure of connectivity in a brain that can be derived from the output of diffusion tensor imaging. Fractional anisotropy data represents a degree of anisotropy (directionality) of a diffusion process. Therefore, fractional anisotropy provides a good approximation of location and dimensions of white matter tracts in a mammalian brain. The fractional anisotropy computation module 52 provides fractional anisotropy data referenced to the reference coordinate system of the semantic network.

In examples, a structural connectivity matrix generator 54 is provided. The structural connectivity matrix generator 54 calculates, for a first plurality of nodes of a subject brain, or portion of the subject brain, the strengths of the structural connections between a second plurality of nodes of the subject brain.

In examples, the PET data output from the PET input imaging workflow 42d is processed by the glucose metabolism module 56 to obtain glucose metabolism information referenced to the reference coordinate system of the semantic network.

The data in the semantic network (knowledge model) provided by the input imaging workflows 42a, 42b, 42c, 42d and processing modules 48, 50, 52, 54, 56 may therefore be provided to a topographical data module 58 in a unified feature space, to enable semantic searching using search terms, for example, provided with reference to a brain atlas such as the Cradock Atlas.

The round arrow in the topographical data module 58 represents an optional continuous update performed by the semantic network. As public databases and/or research results, private diagnostic information, and the like are added or removed from the semantic network 30, the topographical data module 58 respectively enriches or reduces the enrichment of the topographical data of the subject brain. For example, the topographical data module 58 can be considered to be a "brain structure repository" enriched and continually updated with links to available data from external data sources.

Data enrichment module 64 provides sources of public or private data that may be linked or incorporated into the topographical data of the subject brain using the topographical data module 58.

For example, an optional brain atlas module 70 enables portions of the topographical data to be isolated based on textbook definitions of brain regions. An optional functional ontology module 72 and/or an optional anatomical ontology 74 are provided by the semantic network 30, however many other enrichment sources may be linked and used to enrich the topographical data of the subject brain using the data enrichment module 64.

A user interface module 60 of the semantic network 30 enables configuration as lateral selection of the previously discussed modules of the semantic level to be performed.

The user interface module 60 is used to select output modalities. For example, a computer report, a web interface, and/or a printed paper report comprising diagnostic conclusions of the enriched topographical data can be provided for the use of a medical professional.

The user interface module 60 enables selection of one or more patients, brain areas, white matter tracts of the patient's brain. The user interface module 60 may enable selection of outputs such as functional activation, structural connectivity, functional connectivity, structural integrity of white matter tracts (using fractional anisotropic) and glucose metabolism. Furthermore, the user interface module 60 may enable selection of results from brain subnetworks based on 3D location and/or 3D brain atlas information.

According to the semantic network discussed herein, an additional element in the semantic network is generated by the topographical data module 58. An example is, the data comprised in the additional element relies on a query input into the semantic network 30. The data comprising the additional element may be as simple as a likelihood of a patient presenting with a certain disease, such as Multiple Sclerosis, and an indication of the staging of the disease. Alternatively, the data comprising the additional element may include graphical annotations (for example, brain connectivity diagrams) or more complicated statistical connectivity metrics. The data provided in the additional element in the semantic network is, in examples, filtered based on a user sophistication level. For example, more advanced statistical and imaging output modalities may be restricted to research. Simpler information may be comprised in the additional element output by the semantic network 30 in the case that the semantic network 30 is used for, for example, patient triage.

In examples, the semantic network 30 comprises a statistics module enabling large-scale statistical analysis (for example, using a link to the "R" statistical analysis tool, and/or MATLAB™.

In examples, the semantic network 30 comprises a control module 68. The purpose of the control module is to monitor the execution of one or more of the modules of the semantic network 30 to ensure efficient operation and utilisation of hardware resources.

For example, the control module 68 is configured to continually assess the computational intensity placed on one or more computational elements (such as a server in a server farm, or one out of plurality of a set of parallel processes) by the operation of the semantic network 30. In examples, the control module 68 can organise the parallel and/or serial execution of the other modules comprised in the semantic network 30.

In examples, the control module 68 is configured to predict one or more computational loads caused by a user request via the user interface module 60, and to schedule operation of elements of the semantic network 30 to optimise a figure of merit such as latency, energy efficiency, and the like.

In examples, the control module 68 is configured to identify a fault condition of the semantic network 30. For example, the control module 68 may identify a static, dynamic, or essential race condition between any of the modules of the semantic network 30.

In examples, the control module 68 is configured to apply security protocols to one or more of the other modules of the semantic network 30. For example, the user interface module 60 may prompt a user, via a graphical user interface, for a password or indication of a security level of the user of the semantic network. Initial cranial image data of a subject input into the semantic network can also be assigned a security level. If the control module 68 concludes that the current user of the semantic network 30 does not own the security privileges required for access to sensitive classes of patient data, the control module may remove, encrypt, or block access to, sensitive classes of patient data, such as input cranial image data of the subject, from the semantic network.

In examples, the control module 68 is configured to provide quality control of the initial cranial image data and/or the topographical data.

In examples, the semantic network 30 is configured to provide image segmentation of the initial cranial image data and/or the topographical data.

In examples, the semantic network 30 is configured to perform automated nonlinear transformation of the brain from individual to standardised coordinate frames for any imaging modality.

In examples, the semantic network 30 is configured to perform automated parcellation of initial cranial image data and/or topographical data from MRI image data using a brain atlas comprised in the semantic network.

In examples, the semantic network 30 is configured to perform automated parcellation of initial cranial image data and/or topographical data from PET image data using a brain atlas comprised in the semantic network.

In examples, the semantic network 30 is configured to perform automated generation of connectivity matrices from DTI data of the subject. In examples, the semantic network is configured to perform automated generation of connectivity matrices from fMRI data of the subject. In examples, the semantic network is configured to automatically co-register one or more of MRI image data, DTI image data, fMRI image data, and PET image data to the same coordinate frame.

In examples, the semantic network 30 is configured to map initial cranial image data and/or topographical data to multiple brain atlases.

In examples, the semantic network 30 is configured to Annotate topographical data of a subject brain with anatomical, functional, and molecular biological meta data.

In examples, the semantic network 30 is configured to extract anatomical and functional subnetworks of the topographical data automatically. In examples, the semantic network 30 is configured to compute volumetric information of sets of brain areas, or subsets of brain areas, of the subject.

In examples, the semantic network 30 is configured to compute density and/or fractional anisotropic data of white matter tracts in the subject brain.

In examples, the semantic network 30 is configured to obtain high-resolution structural connector models of individual subjects using DTI data.

In examples, the semantic network 30 is configured to obtain a cross-modal comparison between any two types of image of a subject brain from the list of image types: MRI, fMRI, DTI, CT, PET, or PET-CT.

In examples, the initial cranial image data comprises structural MRI data, and the at least one processing sequence comprises a structural MRI data processing workflow.

In examples, the initial cranial image data comprises MRI data, and the at least one processing sequence comprises a functional MRI data processing workflow.

In examples, the initial cranial image data comprises PET data, and the at least one processing sequence comprises a PET data processing workflow.

In examples, the initial cranial image data comprises DTI data, and the at least one processing sequence comprises a DTI data processing workflow.

In examples, the initial cranial image data comprises MEG data, and the at least one processing sequence comprises a MEG data processing workflow.

Connectome-Based Diagnosis

The computer-implemented method according to the second aspect comprises c) comparing the topographical data of the subject brain to one, or more pathological condition prediction elements of the semantic network to form an indication of a pathological condition of the subject.

As noted in the paper "Functional connectomics of affective and psychotic pathology" by Justin T Baker, et al (PNAS, 30 Apr. 2019, vol. 116, no. 18, pp. 9050-9059), functional connectomics can be used to provide insights about the mental condition of a subject.

Given topographical data of the subject (comprising a connectome of the subject, or a portion of the connectome on the subject), comparison of the topographical data of the subject with topographical data related to various mental pathologies can enable an indication of a mental condition to be obtained.

For example, the pathological condition prediction element may comprise topographical data of a control patient known to have a mental condition of interest. By comparing similarities and differences between the topographical data of the subject brain to topographical data of control patient, a diagnosis of the mental condition of interest can be obtained. Additionally or alternatively, a statistical characteristic of the topographical data (connectome) can be compared with a known statistical characteristic of a mental condition of interest.

This concept can be applied over the entire connectome. Alternatively, or in addition, the concept can be applied to specific brain areas.

For example, a user can select a plurality of different brain structures (for example, the brainstem, left cingulate anterior, left inferior temporal posterior, and the like) and select different assessments dependent on the selected type of brain structure.

For example, the user can select assessments of macroscopic brain areas. Alternatively or in addition, the user can select an assessment of connectivity between an arbitrary selection of brain areas that might have clinical meaning in the case of a specific mental condition of interest. For brain areas, the user can select parameters such as volume, and functional activation. For connectivity, the user can choose from assessments for single fibre tracts, whole brain tractography, or selected sub circuits. The assessments for single fibre tracts may be selected from volume and length of the single fibre tract, mean fractional anisotropy, and mean diffusivity.

For whole brain tract and sub-circuit assessment, the user may search one or more quantities such as characteristic path length, clustering coefficient, degree of graph nodes for example.

The techniques discussed herein are not limited to diagnosing MS. Other indications for which connectome biomarker enhanced diagnosis may be provided according to embodiments are epilepsy, migraine, neurodevelopmental disorders, Alzheimer's disease, attention deficit hyperactivity disorder, disorders of consciousness, Parkinson's disease, obsessive-compulsive disorder, depression associated with concussive traumatic brain injury, autism, perinatal hypoxia, amnesia, Tauopathy, post-operative cognitive dysfunction, aphasia and speech of disorders after stroke, schizophrenia, cannabis dependence, fibromyalgia, traumatic brain injury, memory loss, cognitive impairment, fragile X syndrome, anorexia nervosa, white matter disease, depression, concussion, hemi spatial neglect, concussion, dystonia, affective disorders, dyslexia, nicotine dependence, bipolar disorder, chronic pain, stress, coma, neuropathic pain, alcohol abuse, dementia, anxiety, stroke, anxiety disorders, major depressive disorder, traumatic coma, supra nuclear palsy, substance abuse, ageing, frontotemporal dementia, and/or tempo-mandibular disorders.

Selection of Brain Areas for Analysis

The user may apply the semantic network approach discussed above to extract connectivity information within the following brain areas, and/or between any combination of the following brain areas specified, for example, in the Craddock Atlas. In this example, the Craddock Atlas is provided as a element in an instance of the semantic network also comprising topographical data of a subject brain obtained by processing initial cranial image data of a subject according to steps a) and b) of the method.

Connectivity information within or between these brain areas of the subject may be selected by the semantic network and used as a biomarker for mental conditions according to the present aspects:

Brain-stem, cerebellum vermis ix, cerebellum vermis vi, hypothalamus, left angular, left caudate, left central opercular, left cerebellum ix, left cerebellum viib, left cerebellum viiia, left cerebellum viiib, left cingulate anterior, left cingulate posterior, left crus I, left crus ii, Left Cuneous left frontal medial, Left Frontal Operculum left frontal orbital, left frontal pole, left heschl's, left hippocampus, left i-iv, left inferior frontal opercular, Left Inferior Frontal pars opercularis, left inferior frontal pars triangularis, Left Inferior Temporal anterior, left inferior temporal posterior, left inferior temporal temporooccipital, left insular, left intracalcarine, left juxtapositional lobule, left lateral occipital inferior, left lateral occipital superior, left lingual, left middle frontal, left middle temporal anterior, left middle temporal posterior, left middle temporal temporooccipital, left occipital fusiform, left occipital pole, left pallidum, left paracingulate, Left Parahippocampal anterior, left parahippocampal posterior, left parietal operculum, left planum polare, left planum temporale, left postcentral, left precentral, left precuneous, left putamen, left subcallosal, left superior frontal, left superior parietal lobule, left superior temporal posterior, left supramarginal anterior, left supramarginal posterior, left temporal fusiform anterior, left temporal fusiform posterior, left temporal occipital fusiform, left temporal pole, left thalamus, left v, left vi.

Further areas of the brain for which connectivity information within or between these brain areas of the subject may be used as a biomarker for mental conditions according to the present aspects: the right angular, right caudate, right central opercular, right cerebellum viib, right cerebellum viiia, right cerebellum viiib, right cingulate anterior, right cingulate posterior, right crus I, right crus ii, Right Cuneous, right frontal medial, right frontal orbital, right frontal pole, right heschl's, right hippocampus, right I-IV, right inferior frontal opercular, right inferior frontal pars triangularis, Right Inferior Temporal anterior, right inferior temporal posterior, right inferior temporal temporooccipital, right insular, right intracalcarine, right juxtapositional lobule, right lateral occipital inferior, right lateral occipital superior, right lingual, right middle frontal, right middle temporal anterior, right middle temporal posterior, right middle temporal temporooccipital, right occipital fusiform, right occipital pole, right pallidum, right paracingulate, right parahippocampal anterior, right parahippocampal posterior, right parietal operculum right planum polare, right planum temporale, right postcentral, right precentral, right precuneous right putamen, Right Subcallosal, right subcallosal cortex, right superior frontal, right superior parietal lobule, Right Superior Temporal anterior, right superior temporal posterior, right supramarginal anterior right supramarginal posterior, right temporal fusiform anterior, right temporal fusiform posterior, right temporal occipital fusiform, right temporal pole, right thalamus, right v, right vi, vermis vi, or any combination of these.

In examples, native grey matter volume (measured in cubic centimetres), and/or the normalised grey matter volume, and/or the functional activation at rest (Z-score) of any combination or all of the above-listed areas may be used as a biomarker for a mental condition.

In examples, brain connectivity of individual fibre tracts, whole brain tract, selected subcircuits within the above-listed brain areas, and high-resolution intra-area connect, between any combination of the above-listed brain areas may be used as a biomarker for a mental condition.

In particular, individual fibre tracts of particular interest as biomarkers for mental conditions may be selected in the topographical data of the subject using the semantic network. Particular fibre tracts are the Arcuate fasciculi (AF), Supra-genual cingulate bundles (CGC), Uncinate fasciculi (UNC), Inferior longitudinal fasciculi (ILF), Optical radiations (OR), Tracts from the orbitofrontal cortex to the amygdala, Genu of the corpus callosum (GCC), Body of the corpus callosum (BCC), Splenium of the corpus callosum (SCC), and the Cerebral peduncles with the three major corticospinal tracts (CST-L1, L2, L3, R1, R2, and R3). One or any combination of these fibre tracts may be used as a biomarker for a mental condition. In examples, the overall white matter volume (in cubic centimetres), the mean fractional anisotropy, the mean diffusivity, the relative fibre tract density, and the relative fibre tract length, or any combination of these properties of the individual fibre tracts cited may be used as a biomarker for a mental condition.

In examples, the semantic network may perform intra-area connectomics on the cortical brain areas represented in the topographical data. Typically, cortical brain areas may be selected from the FreeSurfer™ "DK Atlas". Specific cortical brain connections that may be selected are between any combination of elements in the list lh.bankssts, lh.caudalanteriorcingulate, lh.caudalmiddlefrontal, lh.cuneus, lh.entorhinal, lh.frontalpole, lh.fusiform, lh.inferiorparietal, lh.inferiortemporal, lh.insula, lh.isthmuscingulate, lh.lateraloccipital, lh.lateralorbitofrontal, lh.lingual, lh.medialorbitofrontal, lh.middletemporal, lh.paracentral, lh.parahippocampal, lh.parsopercularis, lh.parsorbitalis, lh.parstriangularis, lh.pericalcarine, lh.postcentral, lh.posteriorcingulate, lh.precentral, lh.precuneus, lh.rostralanteriorcingulate, lh.rostralmiddlefrontal, lh.superiorfrontal, lh.superiorparietal, lh.superiortemporal, lh.supramarginal, lh.temporalpole, lh.transversetemporal, rh.bankssts, rh.caudalanteriorcingulate, rh.caudalmiddlefrontal, rh.cuneus, rh.entorhinal, rh.frontalpole, rh.fusiform, rh.inferiorparietal, rh.inferiortemporal, rh.insula, rh.isthmuscingulate, rh.lateraloccipital, rh.lateralorbitofrontal, rh.lingual, rh.medialorbitofrontal, rh.middletemporal, rh.paracentral, rh.parahippocampal, rh.parsopercularis, rh.parsorbitalis, rh.parstriangularis, rh.pericalcarine, rh.postcentral, rh.posteriorcingulate, rh.precentral, rh.precuneus, rh.rostralanteriorcingulate, rh.rostralmiddlefrontal, rh.superiorfrontal, rh.superiorparietal, rh.superiortemporal, rh.supramarginal, rh.temporalpole, rh.transversetemporal.

In examples, subsets of brain areas of particular interest as biomarkers for mental conditions are selected in the topographical data using the semantic network by anatomical concept. For example, the biomarkers are defined by connectivity between, and/or connectivity within, the cerebral cortex, frontal lobe, parietal lobe, temporal lobe, occipital lobe, frontal pole, limbic lobe, basal ganglia, cerebellum, cerebellar cortex, cerebellar nuclei, brain stem, Left hemisphere, Right hemisphere, or any combination of these.

In examples, subsets of brain areas of particular interest as biomarkers for mental conditions are selected in the topographical data using the semantic network by concepts that previous investigations have revealed to be linked to functional concepts (see "*Functional connectomics of affective and psychotic pathology*" by Justin T Baker, et al (PNAS, 30 Apr. 2019, vol. 116, no. 18, pp. 9050-9059). For example, the biomarkers are defined by connectivity between and/or connectivity within, the Default mode network, Frontoparietal control network, Limbic network, Salience network, Ventral attention network, Dorsal attention network, Somatomotor network, Visual network, Left hemisphere, and/or Right hemisphere, or any combination of these.

Therefore, the method, in examples, comprises annotating the topographical data with a brain atlas defining brain regions registered to the topographical data in the reference coordinate system, enlarging a formal grammar of the semantic network based on the brain regions defined in the brain atlas; and generating the additional element in the semantic network comprising the indication of the pathological condition of the subject based on a selection of at least one brain region in the brain atlas.

As noted in the introductory discussion about the BioXM™ database, the addition of data into the knowledge model implies the enlargement of the formal grammar of the semantic network. Deletion of data from knowledge model implies the reduction of the formal grammar of the semantic network. The formal grammar of the semantic network may be used for formulating complicated queries concerning the content of the semantic network. Accordingly, if a brain atlas such as the Cradock Atlas (Craddock et al., 2012: Craddock, R. C., James, G. A., Holtzheimer, P. E., Hu, X. P., and Mayberg, H. S. (2012). "*A whole brain fMRI atlas generated via spatially constrained spectral clustering*". Hum. Brain Mapp. 33, 1914-1928. doi: 10.1002/hbm.21333) is comprised as an element within the semantic network according to an embodiment of the method, it is possible to annotate portions of the topographical data of the subject brain using the Cradock Atlas entries (provided the coordinates of the Cradock Atlas are normalised to the referenced coordinate system of the topographical data).

In practice, this means that filtering portions of the topographical data (connectome) of the subject brain using the semantic network becomes as simple for a medical professional as using a graphical user interface (GUI) to select a query from a list in a drop down menu.

In examples, the method comprises annotating the topographical data with a functional and/or anatomical ontology of brain structures defining functional and/or anatomical properties of brain regions registered to the topographical data in the reference coordinate system enlarging a formal grammar of the semantic network based on the functional and/or anatomical ontology of brain regions; and generating the additional element in the semantic network comprising the indication of the pathological condition of the subject based on a selection of at least one brain structure in the functional and/or anatomical ontology.

The Connectome as a Biomarker

The previous section has listed subsets of the topographical data of the subjects brain(connectome) that may be analysed in whole or in part for connectivity. The subsets of the topographical data discussed above can be viewed as "sub- circuits" representable using directed graphs. As such, graph-theoretic statistical concepts can be applied to differentiate and classify these subsets of the topographical data (connectome) of each patient.

Furthermore, a given pathology (such as multiple sclerosis) can be characterised using a graph-theoretic characterisation of one or more of the subsets of the topographical data discussed above.

A pathological condition prediction element of the semantic network is a data structure in the semantic network that may be compared to topographical data of the subject brain in the semantic network to enable the likelihood that a subject is suffering from a specific mental condition, or range of mental conditions, to be provided as an output in an additional element in the semantic network comprising an indication of the pathological condition of the subject.

In examples, one or more subsets of the topographical data in the topographical data of the subjects of brain of interest for a connectome analysis listed above may be assessed by the semantic network using one or more statistical measures, such as clustering coefficient, characteristic path length, small worldness, degree, degree distribution, betweenness centrality, assortativity, modularity, or user-customised statistics.

In examples, the subject connectivity statistic is at least one of associativity, density, modularity, mean of the shortest paths, efficiency, transitivity, weighted characteristic path length, weighted clustering coefficient, or local efficiency of the subject connectivity graph, or a portion of the subject connectivity graph.

The publication "*Homeostatic structural plasticity can account for topology changes following deafferentation and focal stroke*" by Butz et al (frontiers in neuroanatomy, 16 Oct. 2014, doi: 10.3389/fnana.2014.00115) discusses how to characterise weighted characteristic path length, weighted clustering coefficient, small-world parameter, betweenness centrality, local efficiency, global efficiency, and the like in the context of a neuronal graph network, and is hereby incorporated by reference.

In examples, a subject connectivity graph element of the least one topographical data in the semantic network may be provided, wherein the subject connectivity graph element comprises a subject connectivity graph representation of nodes and interconnections between nodes based on functional and/or structural connections between a portion of the subject's brain.

Accordingly, a subset (or the entire) of the topographical data of the subject's brain (connectome) can be characterised using graph-theoretic statistics.

In examples, the method comprises calculating a subject connectivity statistic of the nodes of the subject connectivity graph element; and providing the indication of the pathological condition of the subject by comparing the subject connectivity statistic to a pathological condition prediction statistic.

Furthermore, a pathological condition prediction statistic is, in examples, provided in the semantic network. Thus, for one or more pathological conditions of interest to a clinician, and the variants of the pathological conditions, characteristic example statistics of at least one element topographical data may be provided. For example, the topographical data is topographical control data obtained from one or more previous anonymous patients known to be suffering from the pathological condition of interest to the clinician. If a subject connectivity graph statistic of the subset (or the entire) of the topographical data of the subject brain is compared to a corresponding pathological condition statistic (connectome diagnostic statistic) and the a subject connectivity graph statistic exceeds the pathological condition statistic by a given amount, the semantic network can provide, in additional element in the semantic network comprising the indication of the pathological condition of the subject, the result and/or likelihood that a patient suffering from a given mental condition.

In examples, the method comprises obtaining at least one template connectivity graph element representing a pathological condition, wherein the template connectivity graph element comprises an idealized, averaged, control, or measured template connectivity graph indicative of a brain, or portion of a brain wherein the template connectivity graph is indicative of a neurological condition;

comparing, within the semantic network, portions of the template connectivity graph with corresponding portions of the subject connectivity graph representation;

identifying similarities of the template connectivity graph and the corresponding portions of the subject connectivity graph representation;

providing the indication of a pathological condition of the subject if the similarities of the template connectivity graph and the corresponding portions of the subject connectivity graph exceed a threshold.

According to this alternative diagnostic approach, a graph of the topographical data of the subject brain (connectome) may be generated. A template connectivity graph element is obtained that is a graph representation of the entirety, or subset, of topographical data (connectome) of a control subject brain. For example, one or more control graphs representing the graph characteristics of a control subject suffering from multiple sclerosis or Alzheimer's may be obtained. Therefore, the semantic network may compare, at a graph connectivity level, the connecting of a known sufferer of mental condition with a presenting patient, and provide a likelihood that the presenting patient is suffering from a specific mental condition.

Alternatively, the template connectivity graph element is a synthetic graph representation generated according to a template connectivity script for a specific condition provided in the semantic network. In examples, template connectivity scripts for identifying various mental pathologies may be automatically uploaded to the semantic network reflecting advances in neuroscientific research, for example.

In examples, the subject connectivity statistic and/or template connectivity graph characterizes multiple sclerosis or Alzheimer's disease.

Use of Presenting and/or Historical Symptoms for Analysis

In a busy clinical context, a clinician may be presented with a patient having one or more symptoms (either from a patient history, or symptoms that at the moment of examination). By obtaining at least one set of initial cranial image data of the subject, and inputting a set of one or more symptoms into the semantic network either presenting, or from the patient history, it is possible according to the present method and other aspects to make a useful and specific diagnosis in a short space of time (for example, the amount of time required to process the initial cranial image data into a patient-specific connectome).

In examples, symptoms input into the semantic network may comprise one or more motor symptoms and be taken from the list of: Tremor, Rigor, Akinese, Dys/Hyperkinesia, Diadochokinese, Ataxia, Spasticity and weakness in voluntary movement, Abnormal eye movements (Nystagmus), Unilateral: left, Unilateral: right, Bi-lateral.

In examples, the symptoms may be one or more neurological symptoms, taken from the list of: Fatigue, Neuropathic pain or Sexual dysfunction.

In examples, the symptoms may be one or more symptoms representative of cognitive decline, and taken from the list of Learning, Verbal memory, Visual memory, Recall of new information, Speed of information processing, Visuospatial abilities, Reasoning, problem solving, and planning, and Performance accuracy.

In examples, the symptoms may be symptoms of mental disorder, Primary psychotic disorder, Schizophrenia, Schizoaffective disorder, Primary affective disorder without psychosis, Bipolar disorder without psychosis, or Unipolar depression.

In examples, the method comprises obtaining symptom data and/or input classification data of the subject from the input interface, and incorporating the symptom data into the knowledge model comprised within a semantic network stored in a memory, and forming the indication of the pathological condition of the subject in the semantic network using the symptom data and the at least one element comprising topographical data.

In examples, the method comprises selecting a subset of the topographical data of the subject's brain based on the symptom data, and in examples a brain atlas comprised in the semantic network, and forming the indication of the pathological condition of the subject based on the subset of the topographical data and/or the symptom data.

In examples, the method comprises obtaining risk factor data from the input interface, and incorporating the risk factor data into the knowledge model comprised within the semantic network stored in a memory, and forming the indication of the pathological condition of the subject in the semantic network using the risk factor data.

In examples, risk factor data comprises one or more from the set: later age of onset (patient is older than 35 years), male sex, multifocal onset, efferent system involved, significant disability after five years, high relapse rate in the first 2 to 5 years, abnormal MRI or high MS lesion load, and potential genetic factors. The risk factors of this embodiment tend to indicate a more pessimistic prognosis.

In examples, risk factor data comprises one or more from the set: earlier age of onset, female sex, onset with isolated or sensory symptoms, full recovery after first relapse, long interval after second relapse, limited or no disability after five years, normal MRI/low MS lesion load. The risk factors of this embodiment tend to indicate a more optimistic prognosis.

Progressive Monitoring

In a clinical context such as an outpatient clinic, the subject (patient) may present to a medical professional on multiple occasions, enabling progressive tracking of treatment of the subject's mental condition.

A progressive relapsing disease course affects approximately 5% of multiple sclerosis patients. It is characterised by a steady progression of neurological dysfunction from onset, with clear evidence of acute relapses.

In examples, a subsequent cranial image of the subject is be obtained in a second, third, or further medical imaging step. The initial cranial image data is obtained at a first-time index. The subsequent cranial image is obtained with a second time index. The subsequent cranial image is input into the semantic network specific to the subject. Therefore, an evolution of topographical data of the subject brain between the first and second time indices can be tracked, visualised, and summarised in the statistics. For example, a rate of change of any of the subject connectivity statistics discussed above for any portion of the topographical data can be tracked.

In examples, the method comprises obtaining the initial cranial image data of the subject at a first time index defining an acquisition time of the initial cranial image data; and obtaining subsequent cranial image data of the subject from the input interface at a second time index and incorporating the subsequent cranial image data into the knowledge model comprised within the semantic network stored in the memory and performing steps b), c), and d) on the subsequent cranial image data using the semantic network to thus generate a further additional element in the semantic network comprising a further indication of the pathological condition of the subject at the second time index. Furthermore, the method comprises comparing the additional element and the further additional element in the semantic network to identify a change in the pathological condition in-between the first time index and the second time index.

A number of connectivity plots provided as an additional element in the semantic network comprising an indication of a pathological condition of the subject are now discussed. The connectome information used as the basis for generating the figures of the present specification is based on measured connectome information publicly available from "The Human Connectome Project", by Jesse A. Brown, Jeffrey D. Rudie, Anita Bandrowski, John D. Van Horn, Susan Y. Bookheimer, as discussed in the publication "The UCLA Multimodal Connectivity Database: A web-based platform for connectivity matrix sharing and complex network analysis" (2012), Frontiers in Neuroinformatics, 2012;6:28.doi: 10.3389/fninf.2012.00028.http://dx.doi.org/10.3389/fninf.2012.00028). The measured connectome information was processed using the semantic network according to aspects and embodiments discussed in this specification.

Figure 13:
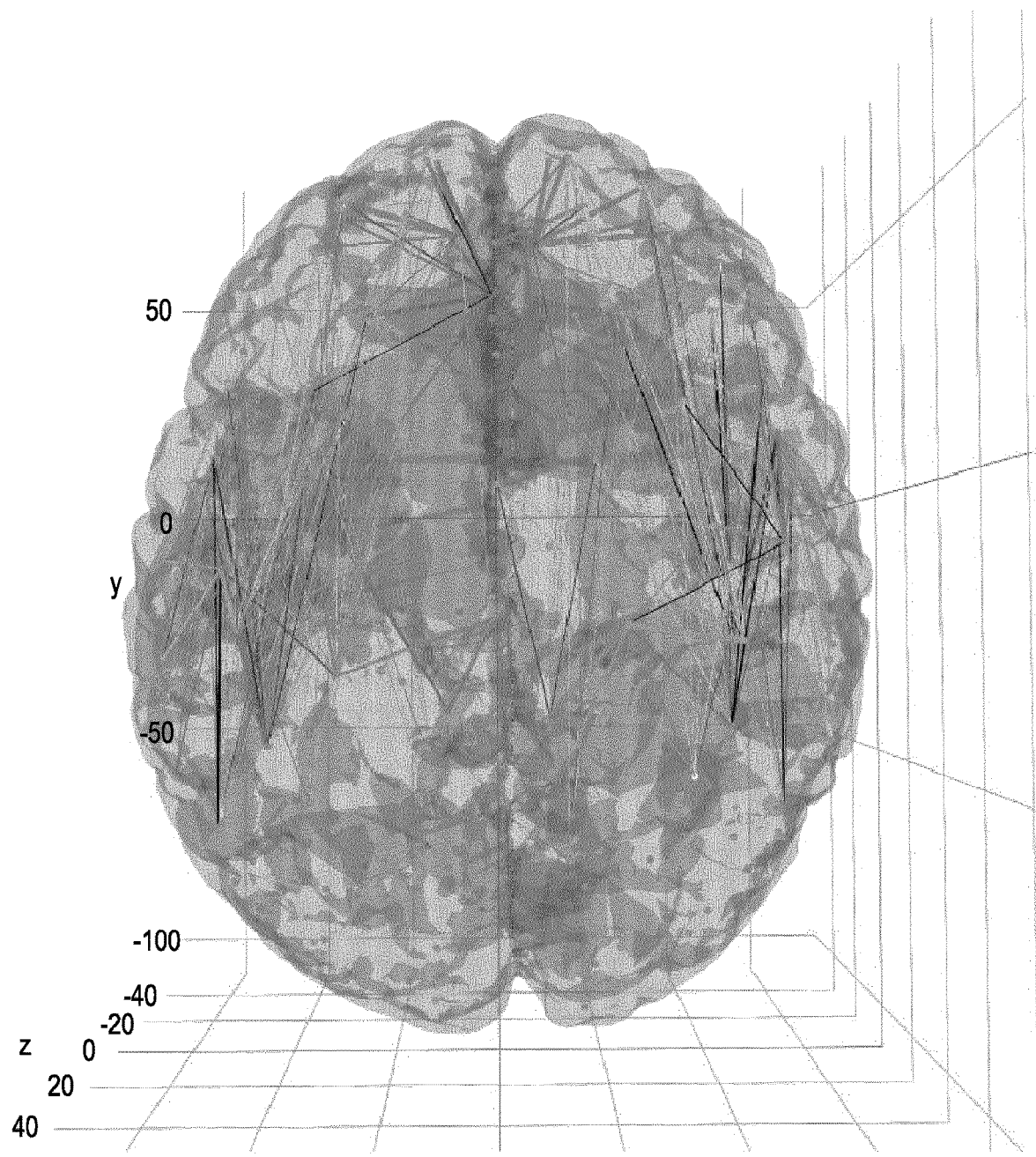
FIG. 13 illustrates an output image of a patient with mild degeneration of white matter tracts in the frontoparietal network.

FIG. 13 illustrates an output image of a patient with mild degeneration of white matter tracts in the frontoparietal network. The frontoparietal network, responsible for higher cognitive tasks, has been affected relatively lightly at this early stage of disease.

Figure 14:
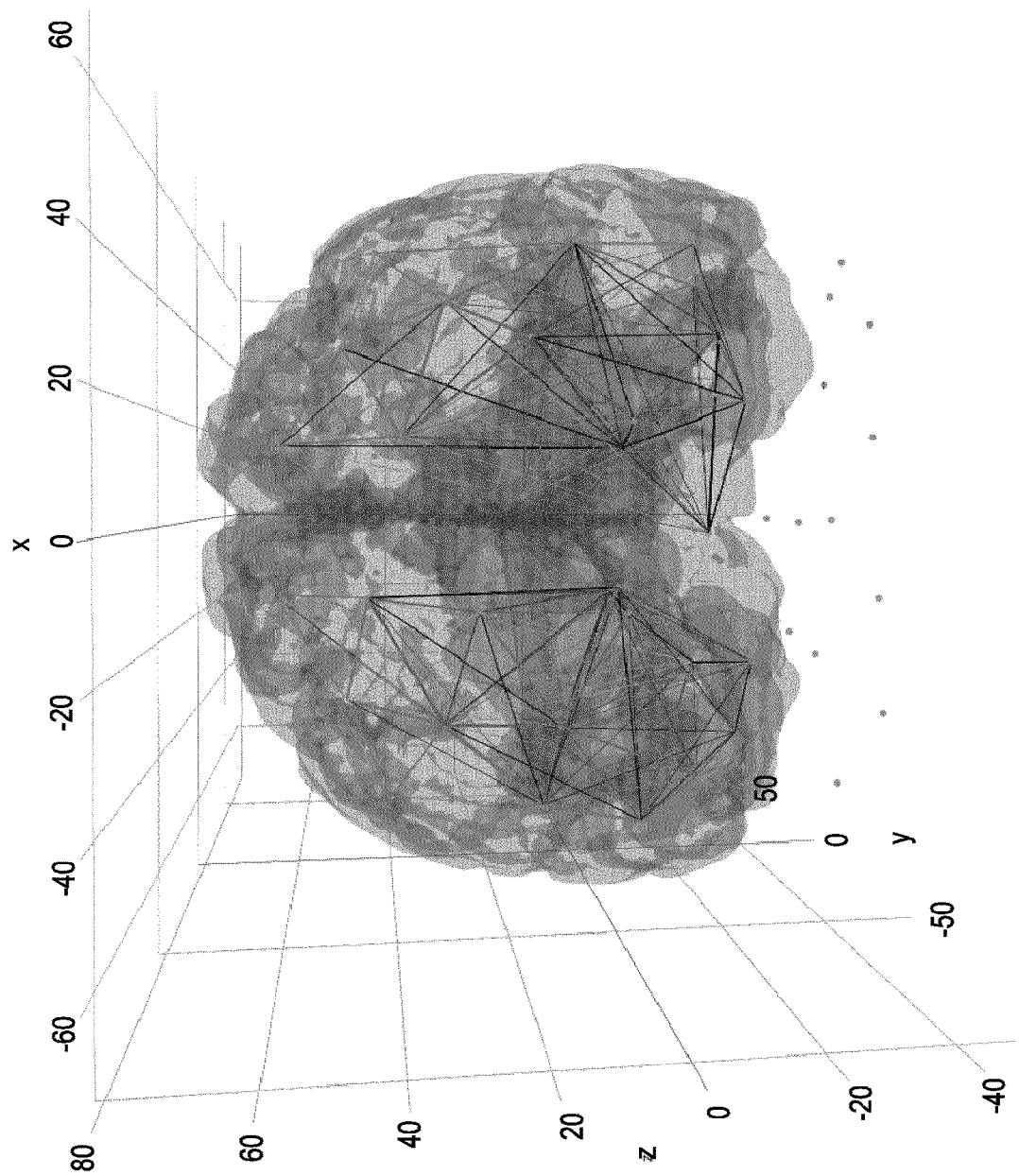
FIG. 14 illustrates the same patient as in FIG. 13 having mild degeneration of white matter tracts in the visual network.

FIG. 14 illustrates the same patient as in FIG. 13 having mild degeneration of white matter tracts in the visual network. The visual network shows a few strongly degenerated fibres at this early stage of disease, which may cause impairments of the visual system.

Figure 15:
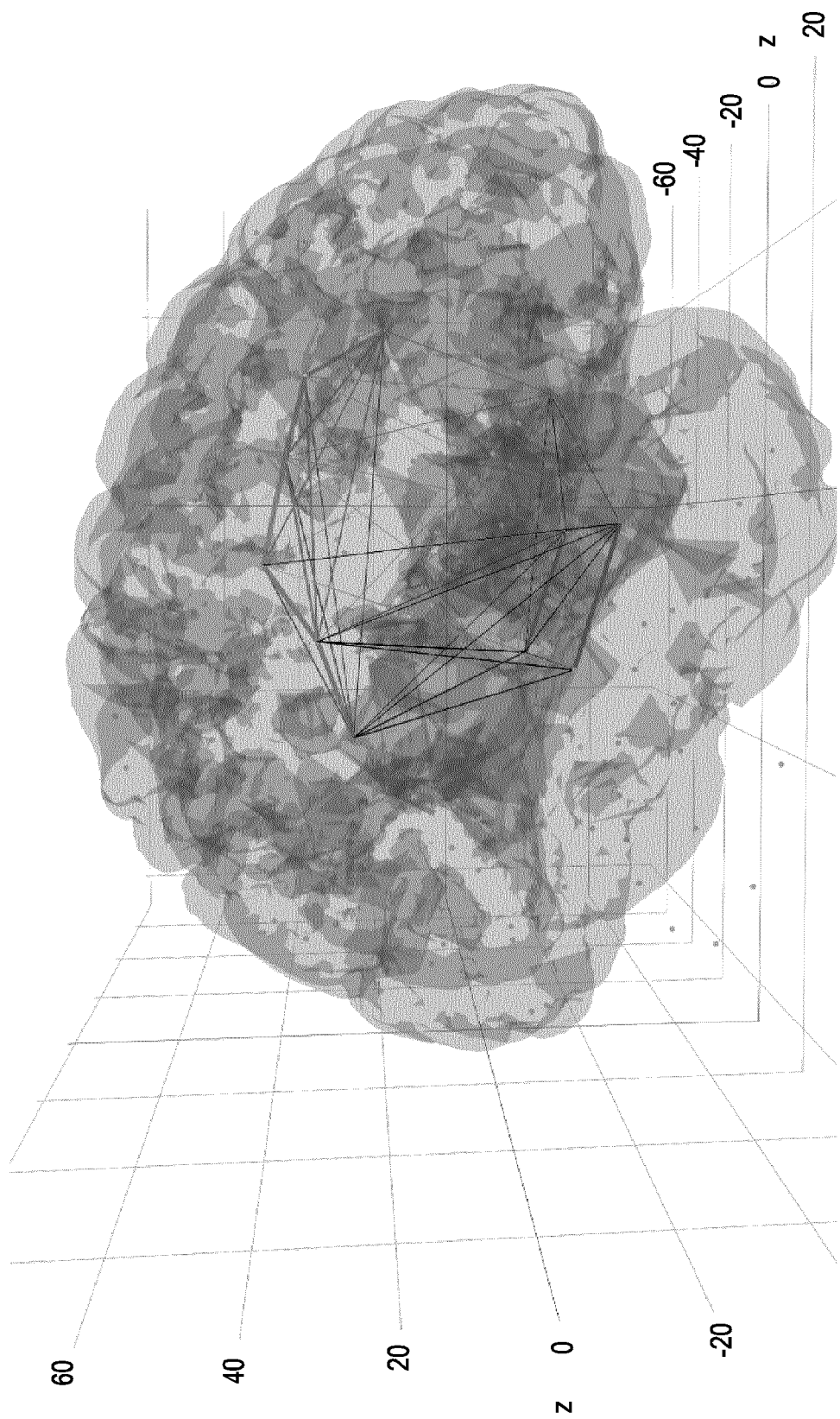
FIG. 15 illustrates the same patient as in FIGS. 13 and 14 having mild degeneration of white matter tracts in the limbic network.

FIG. 15 illustrates the same patient as in FIGS. 13 and 14 having mild degeneration of white matter tracts in the limbic network. The limbic network, responsible for emotional processing, spatial navigation and declarative memory, shows a few strongly degenerated thinner fibres at this early stage of disease, which may be of lower clinical impact.

Figure 16:
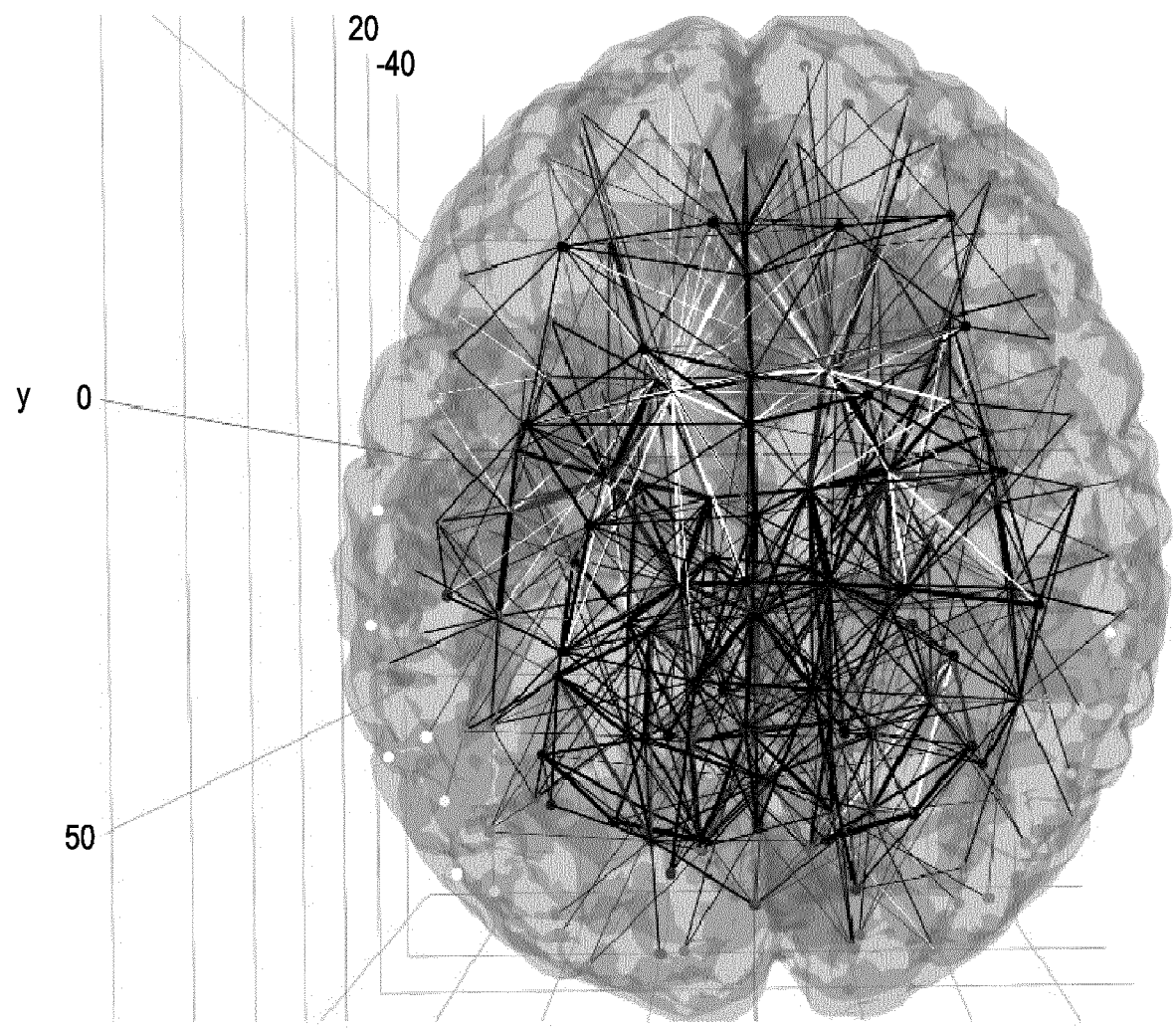
FIG. 16 illustrates an output image showing the connectome of a patient at the transition from relapse-remitting form of MS towards the secondary progressive form of MS.

FIG. 16 illustrates an output image showing the connectome of a patient at the transition from relapse-remitting form of MS towards the secondary progressive form of MS. A significant amount of the white matter white matter tracts have already degenerated so strongly that some cortical areas are connected below the detection threshold of 0.1 relative to the maximum connection strength. Also discernible are a number of grey matter locations at risk of becoming apoptotic. Grey matter lesions are signs of secondary progressive forms of MS and are in general a stronger predictor of more severe clinical disability than whiter matter lesions alone. The line strengths indicate structural connectivity in terms of lines running between two points of interest. The grayscale level of the lines indicates functional connectivity between two points of interest in terms of activity correlations of those locations over time.

Figure 17:
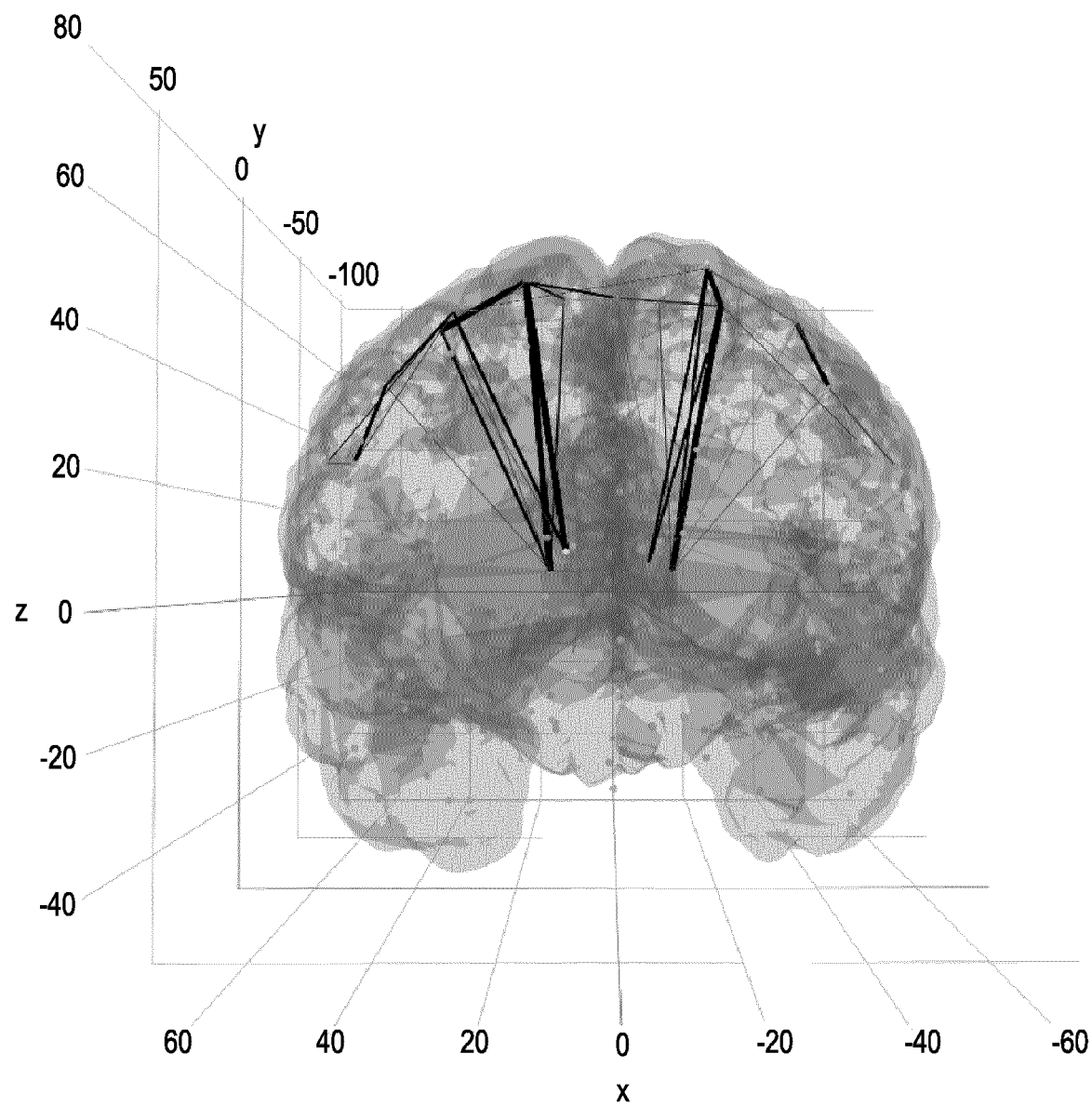
FIG. 17 illustrates a further output image showing the somatosensory-motor system connectome of a patient at the transition from relapse-remitting form of MS towards the secondary progressive form of MS.
Figure 18:
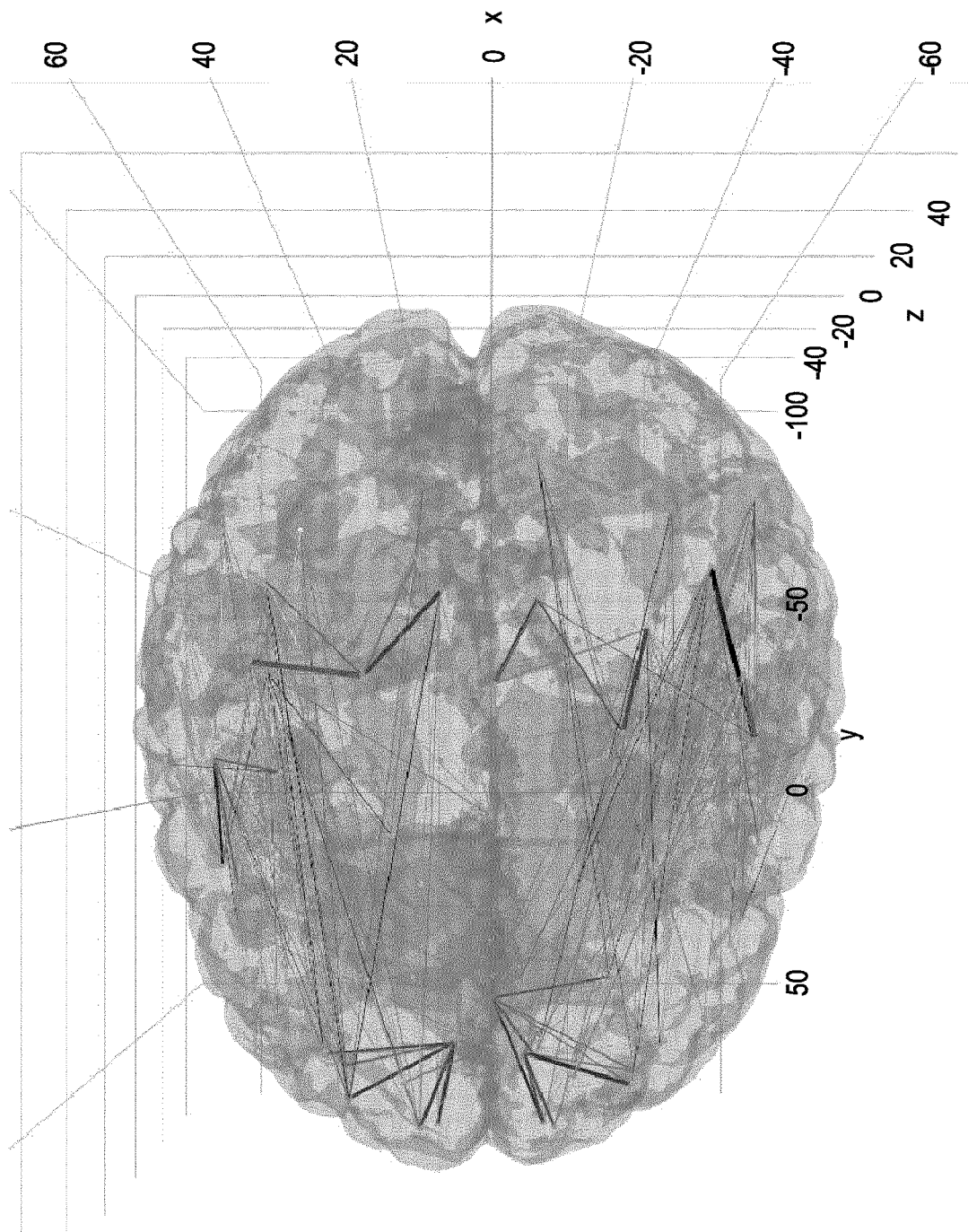
FIG. 18 illustrates a further output image showing the fronto-parietal network connectome of a patient at the transition from relapse-remitting form of MS towards the secondary progressive form of MS.
Figure 19:
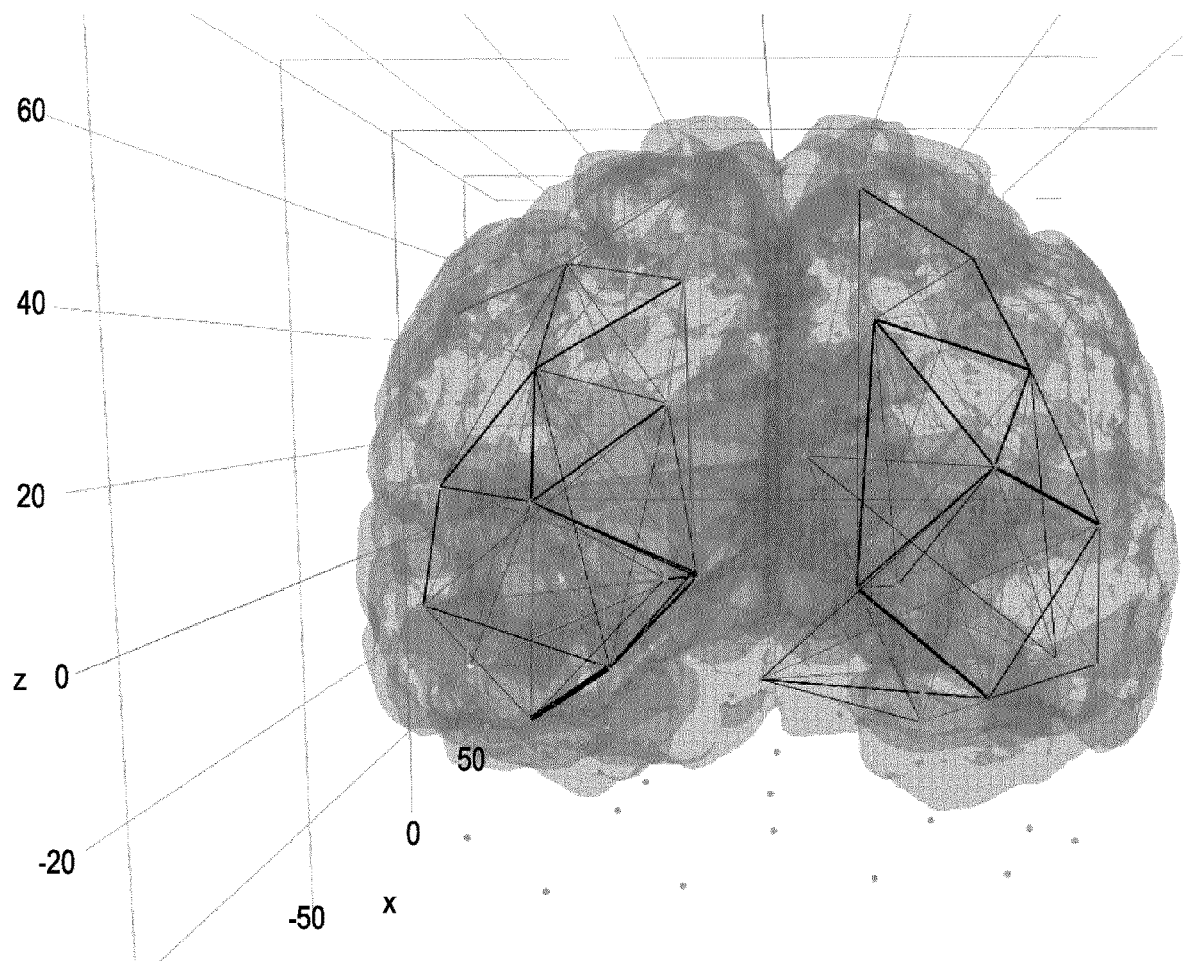
FIG. 19 illustrates a further output image of the visual system connectome of a patient at the transition from relapse-remitting form of MS towards the secondary progressive form of MS
Figure 20:
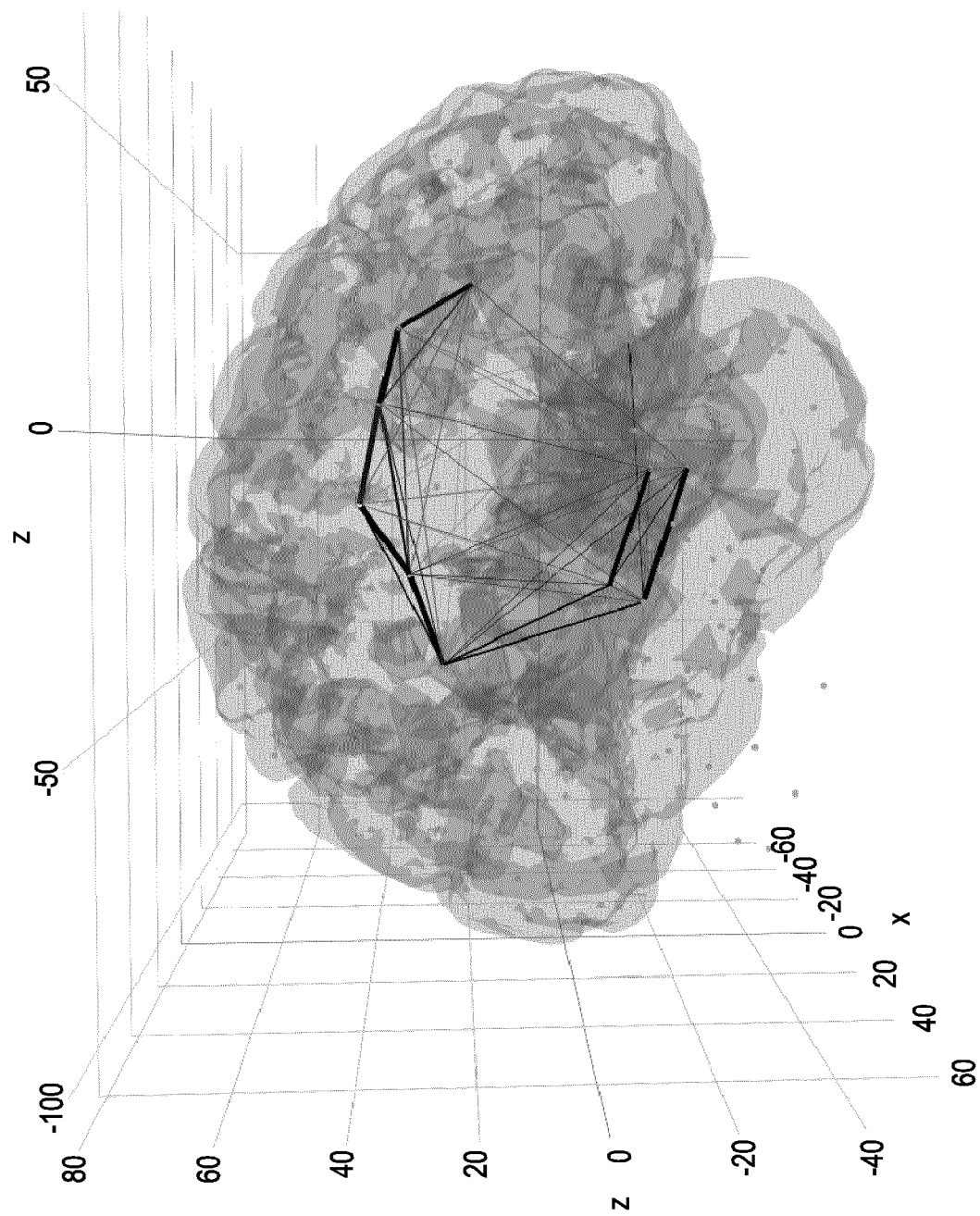
FIG. 20 illustrates a further output image of the patient at the transition from relapse-remitting form of MS towards the secondary progressive form of MS. The figure shows only those connections belonging to the limbic system.

FIG. 17 illustrates a further output image showing the somatosensory-motor system connectome of a patient at the transition from relapse-remitting form of MS towards the secondary progressive form of MS. The somatosensory-motor system is affected, which may cause significant motor deficits FIG. 18 illustrates a further output image showing the fronto-parietal network connectome of a patient at the transition from relapse-remitting form of MS towards the secondary progressive form of MS. The fronto-parietal networks are affected but not as strongly as the motor network. Cognitive deficits may be expected to a certain degree FIG. 19 illustrates a further output image of the visual system connectome of a patient at the transition from relapse-remitting form of MS towards the secondary progressive form of MS. The visual system is strongly affected and may cause significant impairments of the patient's ability to see or to perceive visual scenes. FIG. 20 illustrates a further output image of the patient at the transition from relapse-remitting form of MS towards the secondary progressive form of MS. The figure shows only those connections belonging to the limbic system. The limbic system is increasingly affected. Especially fibres originating from hippocampal areas show significant degeneration potentially causing memory deficits in the patient.

Tables comprising sample values generated by the semantic network according to aspects extracted from of the connectome diagrams of FIGS. 13 to 20 are provided at the end of the specification.

Simulation of Future Progression

The publication "*Homeostatic structural plasticity can account for topology changes following deafferentation and focal stroke*" by Butz et al (frontiers in neuroanatomy, 16 Oct. 2014, doi: 10.3389/fnana.2014.00115) discusses modelling of the future evolution of a brain network using the model of structural plasticity.

Given topographical data of a subject brain, it may be desirable to model the future development of the connectome, or a subset of the connectome. In some cases, a subject brain may be able to repair or to reorganise around a lesion, for example. In other cases, a subject brain may enter a stage of irreversible breakdown following the appearance of a lesion. In a disease such as multiple sclerosis, irreversible breakdown can herald the beginning of the progressive stage of the disease. According to the present embodiment, a brain simulation may be applied to obtained topographical data (connectomic data) from a subject to examine the future development of the connectome. In examples, the semantic network comprises an element capable of executing one or more iterations of the model of structural plasticity on a subset of a topographical data of the subject.

In examples, the method comprises accessing, via or in the semantic network, a neurological simulation element, wherein the neurological simulation element is configured obtain the at least one element comprising topographical data as a starting point of a neurological simulation, and generating a simulated topographical data element in the semantic network as an output of the neurological simulation element applied to the topographical data.

Therefore, the generated additional element of the semantic network may comprise predicted network connectivity statistics defining the evolution of the subject brain at a plurality of time points into the future. In examples, the generated additional element of the semantic network may comprise graph simulations defining the predicted evolution of the connectome or a subset of the connectome of a patient.

Input

An input interface may be provided on a user interface of an apparatus according to aspects discussed herein. The input graphical user interface element 164 may be displayed, for example, on a computer screen of a computer. The primary input to the system is initial cranial image data of the subject (obtained from a PACS server and/or a medical imaging system), however information about other symptoms that a patient is suffering from enable the semantic network 30 to restrict or narrow a search space when reaching a diagnosis using one or more medical images.

In examples, an apparatus may provide a user interface enabling a user to select various restrictions or comparisons that semantic network should perform when assessing the generated topographical data of a patient.

Figure 5:
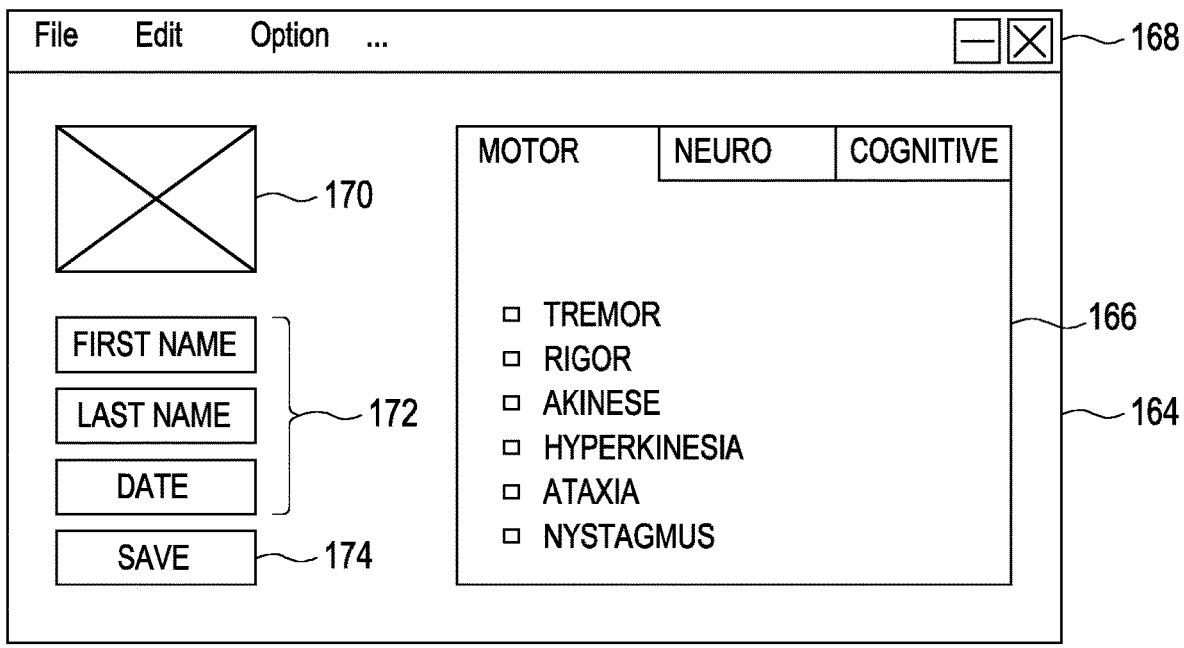
FIG. 5 illustrates a graphical user interface for the input of symptom information.

FIG. 5 schematically illustrates an example of an input graphical user interface element 164 for inputting specific symptoms related to a specific patient into the semantic network 30.

In this example, the graphical user interface element 164 comprises a symptom selection dialog window 166 enabling a medical professional to quickly select one or more qualitative symptoms that a patient is presenting with. A user may input the patient name, patient reference (not shown) and an examination date into fields 172. The semantic network 30 may automatically access a hospital PACS system to populate a patient image field 170. When an initial set of symptoms has been entered, a user may save the details of the examination using save button 174.

It will be appreciated that many different designs and functions of graphical user interfaces for inputting data into the semantic network 30 can be provided.

Output

In a clinical context, useful and clear to understand outputs are important when deciding on recommendations for future treatment and medication of the subject.

Figure 6:
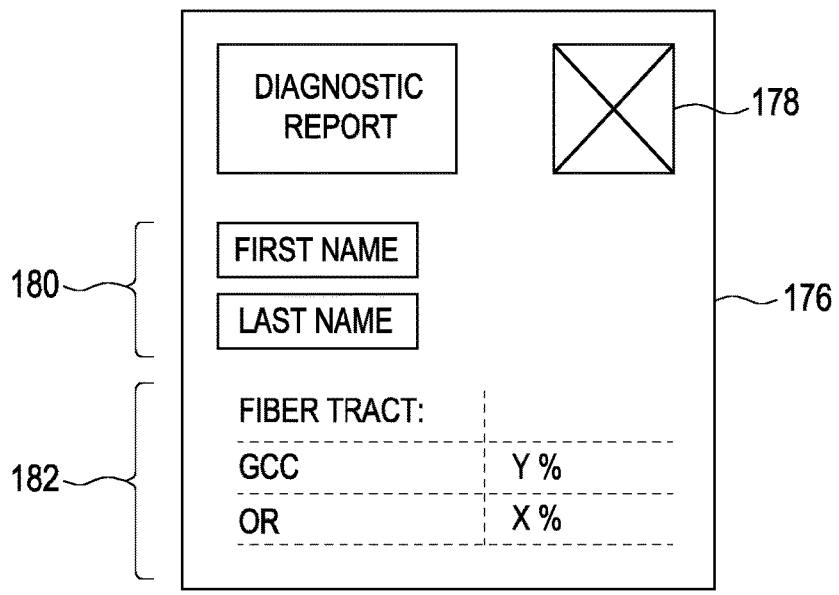
FIG. 6 illustrates an output report generated by the semantic network.
Figure 7:
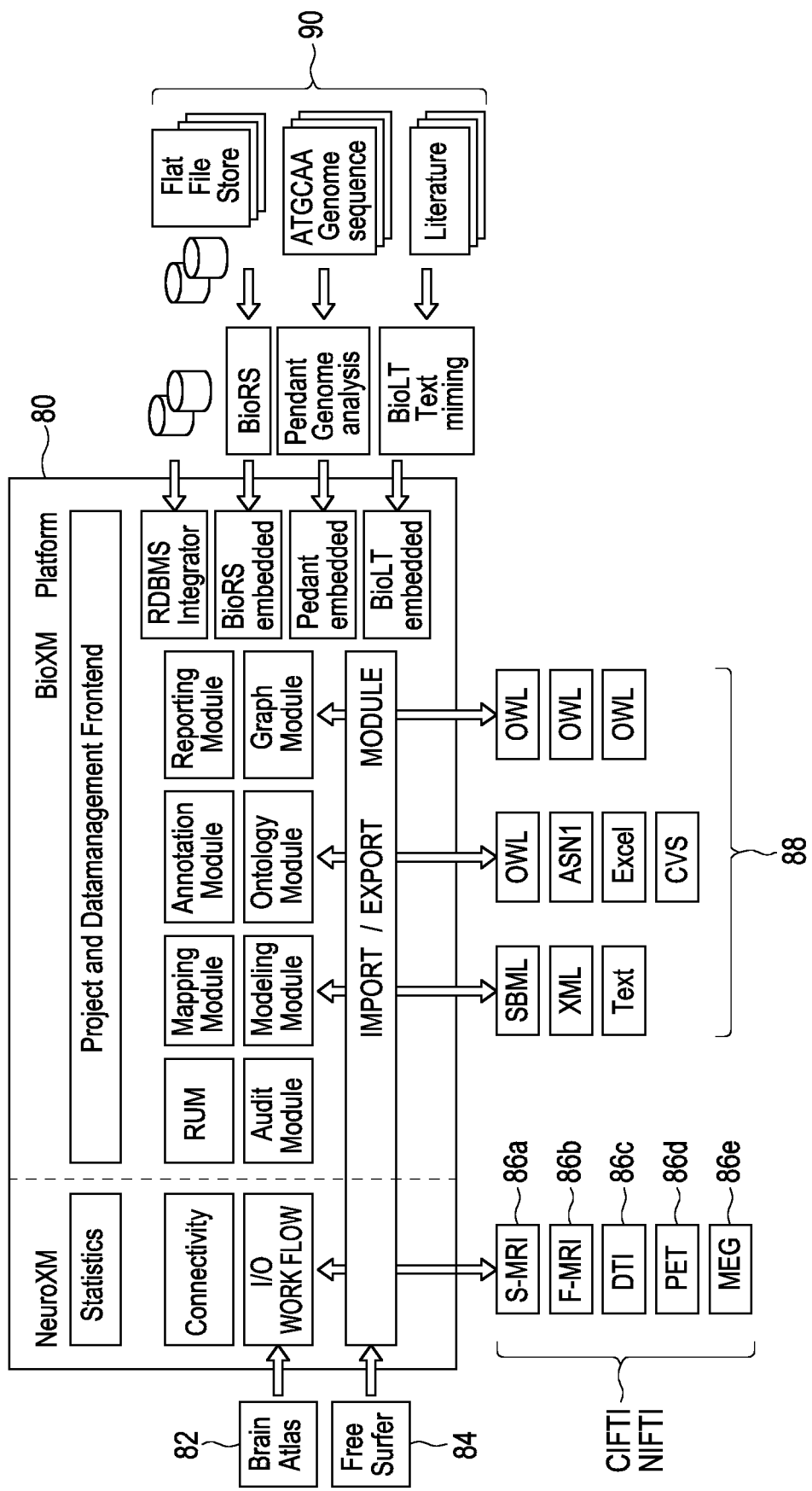
FIG. 7 schematically illustrates the BioXM™ database framework.

FIG. 6 schematically illustrates a simple example of a diagnostic report that may be output by the semantic network 30. The diagnostic report is generated using the data comprised in the additional element in the semantic network comprising the pathological condition of the subject. The simple report format illustrated would be suitable, for example, at the triage stage of a clinic. A reader will appreciate that other, more detailed report formats comprising complicated images and data tables could be provided for medical research professionals, or surgeons, for example.

The diagnostic report 176 comprises an indication of the patient name 180 (and optionally patient reference number), and a summary of the pathological condition of the subject based at least on initial cranial image data input into the semantic network 30. A diagnosis section provides simple likelihoods of pathological indications that can be used, for example, to triage a presenting patient to the correct neurological specialist. In examples, the diagnostic report comprises an image of the patient to ensure that the diagnosis can be verified to an individual.

The diagnostic report can be provided as a printed record, or via a web interface to the semantic network 30 displayed on a computer screen, or a smartphone screen Although not shown, when presented electronically such as via a web interface, the diagnostic report 178 is optionally password-protected, or display of the diagnostic report is otherwise restricted based on a privilege level of a user of the semantic network.

In examples, the method comprises outputting the indication of the pathological condition of the subject based on the additional element in the semantic network.

In examples, the method comprises generating an output image illustrating the intrinsic functional connectivity of the topographical data of the subject's brain and displaying the output image to a user.

In examples, the method comprises receiving a user query, generating a request by transforming the user query into the formal linguistic specification defined by the semantic network; and obtaining an output report to display the indication of the pathological condition of the subject using the additional element in the semantic network based on the user query.

In examples, the method comprises generating output classification data of the subject based on the indication of a pathological condition in the additional element in the semantic network; and outputting a report comprising the output classification data.

In examples, the diagnostic report is provided as a graphical user interface on a computer screen, mobile tablet, smart phone and the like. In examples, the diagnostic report is printed and provided as a paper report.

In examples, more sophisticated output modalities that may be incorporated into diagnostic report comprise representing localisation regions of white matter degeneration and/or grey matter degeneration in an image.

In examples, a comparison of a subject connectome in part or in its entirety with control connectomes of a specific mental condition may be performed. The comparison may be provided as a three-dimensional visualisation in an interactive graphical user interface. For example, a comparison of a subject connectome in part or in its entirety with control connectomes of a control suffering from multiple sclerosis may be performed. In examples, the control connectomes used for the comparison may be filtered for age, sex, and/or IQ characteristics.

In examples, a plurality of brain scans obtained at different time steps may be displayed alongside exemplary subject connectivity statistics.

In examples, selectable detailed reporting can be presented in a graphical user interface or a printed report for selectable brain areas, selectable anatomical and functional brain networks, selectable biomarkers (volume, functional activation, functional connectivity, fractional anisotropy, structural connectivity, complex network measures, and the like).

In examples, metrics illustrating the prediction of remaining brain network stability, integrity, and/or reserve capabilities of patient brain network obtained by brain simulation of a subject brain may be obtained.

Figure 11:
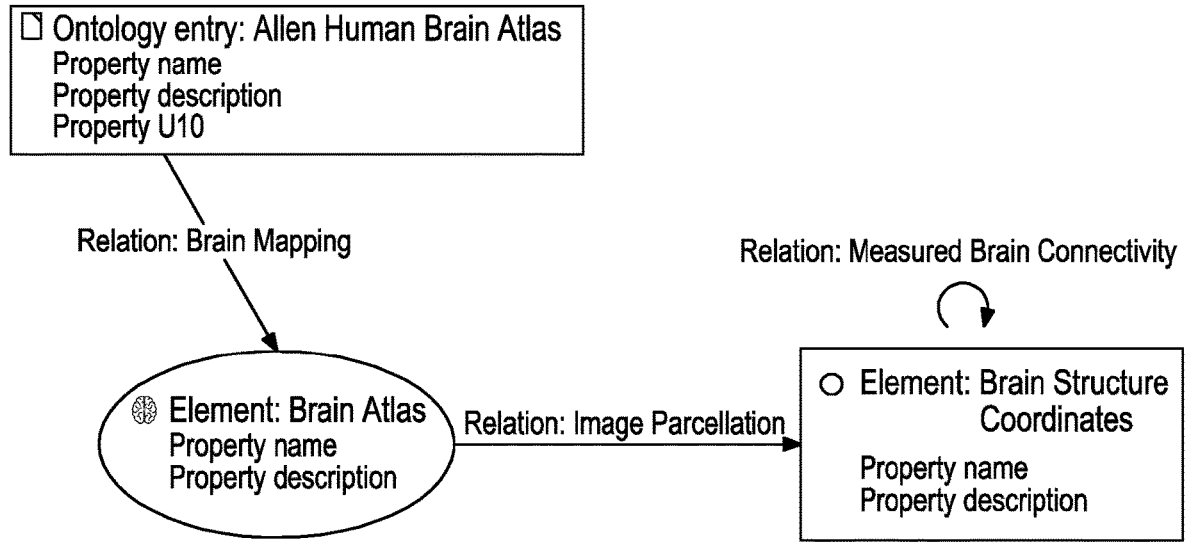
FIG. 11 schematically illustrates examples of graphical user interface elements in the BioXM™ database.
Figure 11:
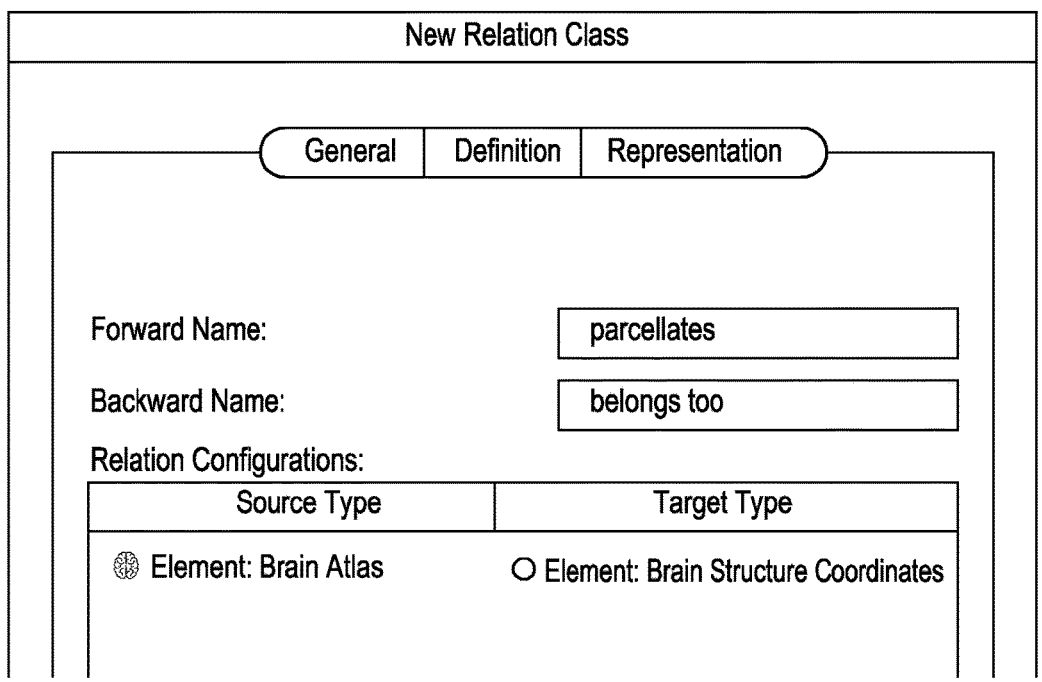

FIG. 11 illustrates an example of a GUI interface to a semantic network 30 between a gene element and a protein element in the BioXM™ database (although it will be understood that the GUI interface can easily comprise elements referring to brain science).

The top part of FIG. 11 illustrates a part of the GUI illustrating the knowledge model graph in the neuroscience domain of the semantic network that can be used to represent brain connectivity. Any location in the brain is represented by a semantic object—an Element "Brain Structure Coordinates".

Structural or functional connectivity that was measured between two locations in the brain by DTI or fMRI, respectively, is represented by the relation "Measured Brain Connectivity". Any location may be enriched with brain atlas information. For this, the element "Brain Structure Coordinates" is related to a brain atlas entry (element "Brain Atlas") via the relation "Image Parcellation". Ontologies such as the Allen Human Brain Atlas are used via the relation "Brain Mapping" to put brain atlas entries in a wider anatomical or functional context.

The GUI shown at the bottom of FIG. 11 illustrates one example of GUI used for defining a semantic network in the BioXM™ database. "Relations" are defined by a forward name and a backward name. For example, the relation "Image Parcellation" relating element "Brain Atlas" to element "Brain Structure Coordinates" is defined by forward name "parcellates" and by backward name "is parcellated by". These natural language terms can then be used for building queries to retrieve information that is stored in databases. For example, one could query for all elements Brain Structure Coordinates which "belong to" a brain atlas entry which is the "frontal pole, right".

Figure 12:
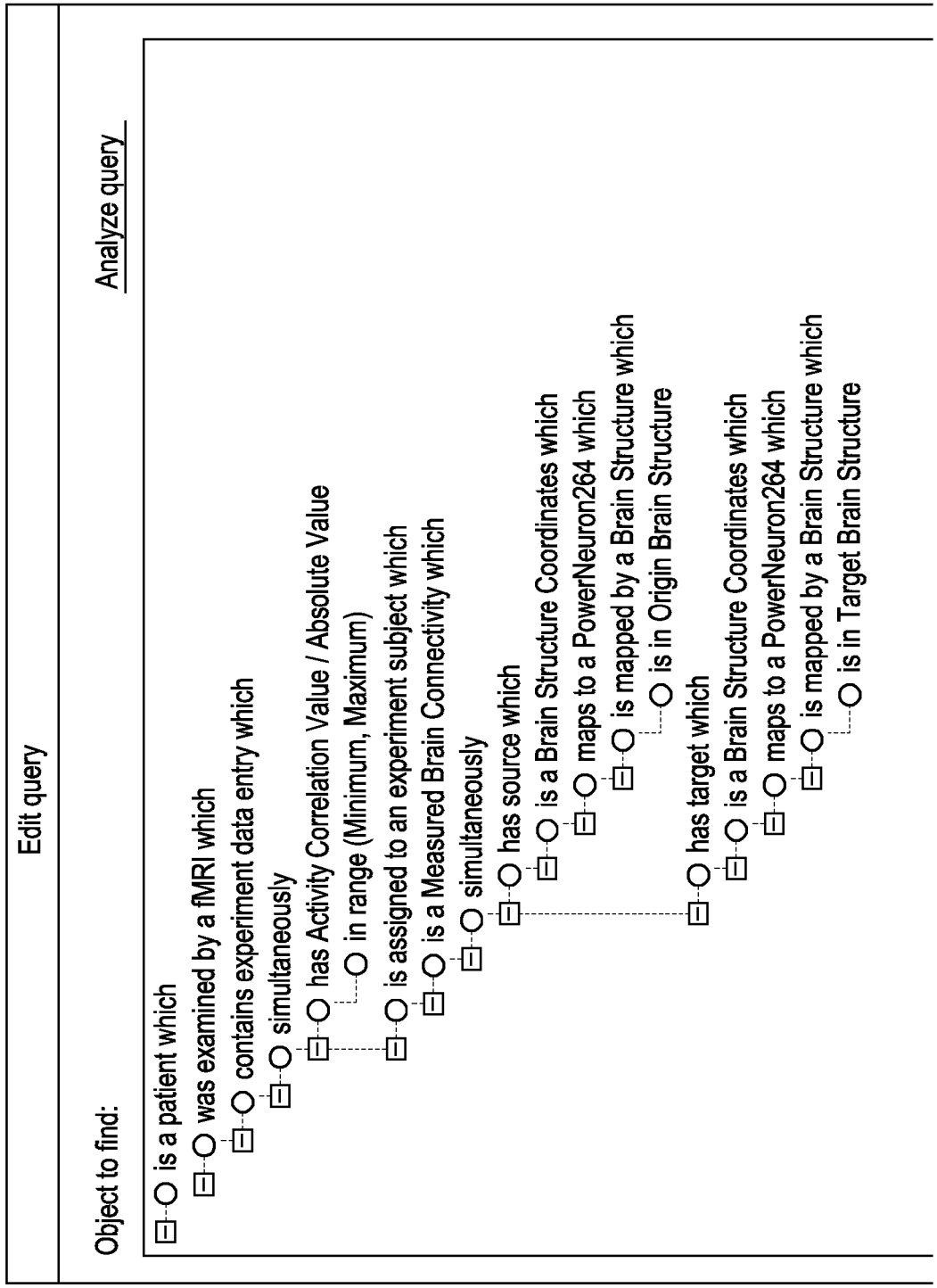
FIG. 12 schematically illustrates an example a graphical user interface of the BioXM (TM) platform that may be used to construct a natural language query using the formal language derived from a semantic network.

FIG. 12 illustrates an example of a natural language query built in a GUI, using the formal language derived from a semantic network 30. The semantic network used to generate the natural language query of FIG. 12 must, in this case, comprise at least an fMRI "experimental" data entry (corresponding to initial cranial image data of the subject), and a brain atlas.

Security

The BioXM™ database is well-suited to providing a secure processing environment for medical data because of the strongly-typed structure of the semantic network. Various elements of the semantic network may be provided with higher or lower security requirements dependent on their relevance to patient data. For example, publicly available gene databases, connectome databases and the like already utilise anonymous data and further security may not be needed, or may only be required at a low level.

Data obtained directly from medical scanning procedures (such as the initial cranial image data) or post-process data (such as the topographical data) are extremely sensitive. Furthermore, any type of indication of a pathological condition of the subject is highly sensitive, and measures must be taken to ensure that the information is well-protected from accidental disclosure, or deliberate theft.

Apart from the usual range of computer security measures such as the use of virus scanning, intrusion detection, firewalls that are familiar to the skilled person, the semantic network itself may be configured to improve security patient data.

In an extreme case, the semantic network is capable of native implementation on a stand-alone computing cluster connected to a medical scanning system at the clinical location. The cluster and the medical scanning system are not connected to an external data communications network. Furthermore, communications interfaces on computers in the cluster and the medical scanning system are electronically disabled. Only staff members with an elevated level of security clearance can load or remove data from the cluster. In such an implementation, it is envisaged that medical image data will be obtained from a medical scanning system, and that the semantic network will process the medical image data in an isolated manner on the computing cluster to obtain an indication of the pathological condition of the subject. Such computing cluster would require between tens and hundreds of terabytes of stored human brain images to provide the necessary template connectivity graph elements of anonymous control cases.

In examples, the semantic network operating on the cluster may isolate patient specific data in an encrypted portion of the semantic network. Then, the semantic network may enable one or more elements of the semantic network that do not comprise patient data to access remote update databases (for example, over the Internet, or using an FTP server).

In examples, the semantic network operating on the cluster may require patient specific data to be deleted from the semantic network, and only enable connection of the cluster to the Internet when patient specific data has been deleted from the cluster.

Alternatively, the semantic network may be operated at a remote location (such as a secure cloud service). Initial cranial image data of the patient may be anonymized and strongly encrypted. Subsequently, the initial cranial image data is transmitted, over a communications network such as the Internet, to the semantic network at the remote location for analysis. An anonymized and strongly encrypted result may be returned from the remote location.

Alternatively, the semantic network may be operated at a remote location in the manner of a blood testing laboratory. Initial cranial data may be loaded onto a tape drive and strongly encrypted, and then physically transported to the remote location for analysis by semantic network operating on a large computer cluster as discussed herein. Results data may be sent back via encrypted email, or secure post.

In examples, the method comprises storing the initial cranial image data and the at least one element comprising a topographical data of the subject's brain, or a portion of the subject's brain, in a segregated subdivision of the semantic network; and performing subsequent processing of the initial cranial image data, or the topographical data, or data derived from them, exclusively within the segregated subdivision of the semantic network; and wherein any subsequent access to the initial cranial image data or the topographical data in the segregated subdivision of the semantic network by an unsegregated portion of the semantic network requires user authentication.

In examples, the method comprises
 obtaining user authentication data from the input interface 22
 verifying, based on the user authentication data, that the user has a security privilege to allowing access to the segregated subdivision of the semantic network; and
 processing at least one of the subject connectivity graph element, the subject connectivity statistic, the additional element comprising the indication of the pathological condition of the subject and/or the indication of a pathological condition in the segregated subdivision of the semantic network; if the user has security privileges to access the segregated subdivision of the semantic network.

In examples, the method comprises:
 encrypting the segregated subdivision of the semantic network,
 wherein decryption of the segregated subdivision of the semantic network requires user authentication.

Figure 8:
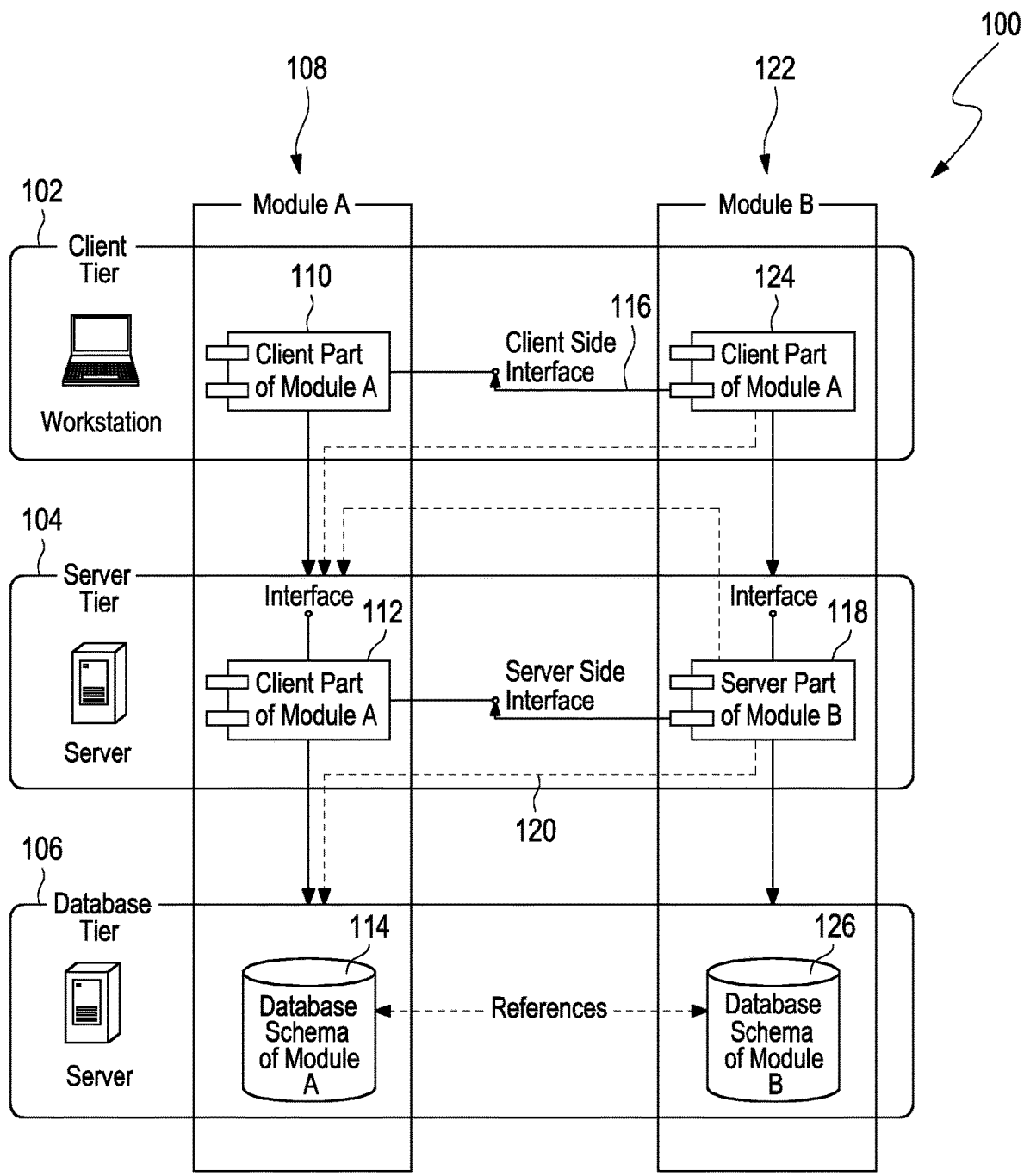
FIG. 8 schematically illustrates tiers and modules of an example implementation of the BioXM™ database.

FIG. 8 schematically illustrates tiers and modules of an example implementation of the BioXM™ database. As explained further in WO 2018/149930 A1, which the reader should now refer, and which is hereby incorporated by reference, the BioXM™ database is implemented with a client tier 102, a server tier 104, and a database tier 106. The database tier 106 comprises a relational database management system (RDBMS) used by the database tier 106. This functions is to ensure the persistence of all data loaded into the semantic network 30.

The RDBMS may take many forms, but should preferably support transactions and provide a database connectivity driver. The RDBMS is preferably supported by "hibernate"™, a domain model for enabling persistence in relational databases. Preferably, the database may be a "MySQL" database, "Maria DB"™ and/or Oracle™, although many other types of RDBMS database system could be used. Alternatively, the database is an object-oriented database.

The semantic network 30 can be implemented using a database running on computer hardware, with associated computer hardware for inputting information and visualising results. In a first variant, a client tier 102, a server tier 104, and a database tier 106 are stored and executed on the same computer equipment.

In a second variant, the client tier 102 is stored and executed on a first computer, and the server tier 104 and the database tier 106 are stored and executed on a second computer, which may optionally be located geographically remotely to the first computer storing and executing the client tier 102. For example, the client to 102 may be accessible via a communications network such as the Internet, or a wired or wireless LAN. The database tier 106 comprises database schema 114 of a first module 108 of the semantic network. The database tier 106 may comprise a second database schema of a second module 122 of the semantic network. For example, the database schema 114 may comprise elements of a structural MRI input processing routine, and the database schema 126 may comprise elements of a Human brain atlas. The database schema of the first and second modules may optionally reference each other.

Figure 9:
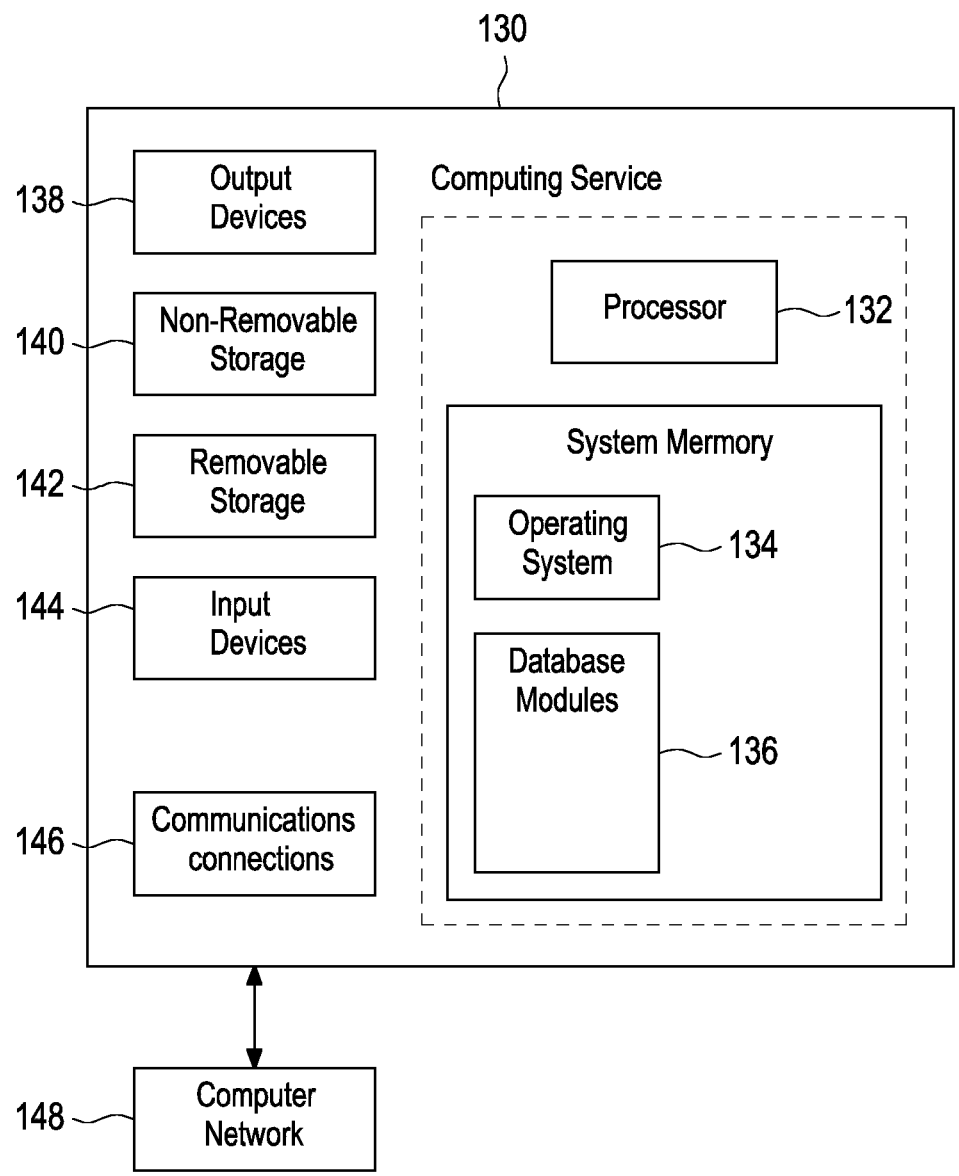
FIG. 9 schematically illustrates a computer implementation of the BioXM™ database.

FIG. 9 schematically illustrates a computer implementation on a computing device 130 of the BioXM™ database. For example, the computing device 130 optionally implements the client tier 102, the server tier 104, and the database tier 106 of the semantic network 30 (knowledge model). Alternatively, the computing device 130 may implement the client tier 10, and communicate with an external computing device (not shown in FIG. 9) which may be of the same general disposition as the computing device 130 be configured to implement the server tier 104 and the database tier 106 of the semantic network 30.

Computing device 130 provides, in a basic configuration, a computing service provided by a processor 132 and a system memory. The system memory may comprise volatile storage, non-volatile storage, flash memory, or a combination of these. Operation of the computing device 130 may result in an operating system being loaded into the system memory.

The operating system may contain database modules enabling operation of the semantic network 30 (knowledge model) discussed herein. Typically, the database modules 108, 126 are implemented using a database accessed using the SQL language, but other database formats will be known to a skilled person. The operating system of the computing device 130 may, for example, be capable of controlling the computing device 130.

The database modules and program files may be held in the system memory. When executing on the processor 132, the database modules may perform processes including, but not limited to, any one of the steps of the method and processes discussed herein or illustrated in the figures.

Furthermore, embodiments of the computing device 130 may be provided as a general purpose computer comprising packaged electrical circuits comprising logic gates, a microprocessor, a general-purpose microprocessor as, for example, supplied by Intel™.

The computing device 130 may also comprise output devices 138, such as a display, a printer, loudspeakers, and the like. The computing device 130 may also have input devices 144 such as a keyboard, mouse, touch screen, or microphone.

The computing device may also comprise a removable storage interface 142 suitable for interfacing with computer readable media. Computer readable media include volatile and non-volatile memory, suitable for storing computer-readable instructions, data structures, and program modules. It may include flash memory, CD-ROM, DVD, DVD-R, other optical storage media, USB memory sticks, magnetic cassettes, magnetic tape, magnetic disk storage such as a removable hard drive, solid-state storage, computer network discs, any of which can be used to store information and be accessible by the computing device 130. The computing device 130 may also have non-removable storage 112 suitable for the operation of the computing device 130 such as RAM, EEPROM, magnetic disk memory, and the like.

The computing device 130 may also have communication connections 146 such as an ethernet interface, Wi-Fi connections, USB, and other interfaces enabling connection of the computing device 100 to an external computer network.

Figure 10:
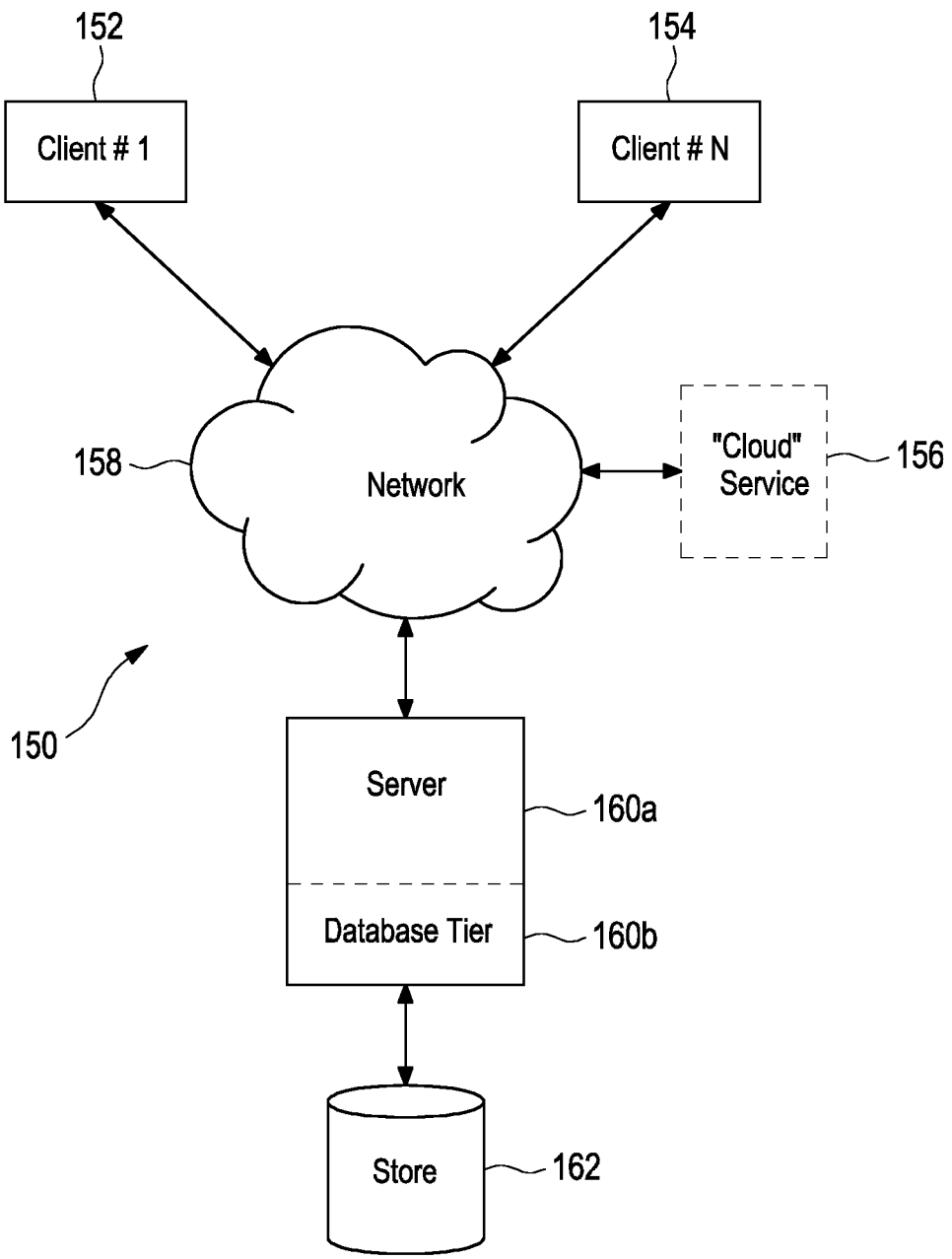
FIG. 10 schematically illustrates a client-server implementation of the BioXM™ database.

FIG. 10 schematically illustrates a client-server implementation of the BioXM™ database 30. In particular, the client-server network 150 comprises a first client 152 and a second client 154 each according to the description in respect of FIG. 9. However, a large number (or only one client) of clients may be supported if necessary. The first client 152 and second client 154 are configured to communicate with a network switching fabric 158 via communication links. The communication links to the network switching fabric 158 may be ethernet connections, Wi-Fi connections, and the like, enabling communication with a distant server 160a, 160b through the network switching fabric 158 using a networking protocol.

Exemplary networking protocols are TCP/IP or UDP, although other protocols will be known to a person skilled in the art. Thus, the network switching fabric 158 may contain, for example, a hierarchy of switches, routers, network servers and the like to ensure that data can be transferred between the client's 152 and/or 154 in a timely manner. The server 160a, 160b may be connected to a data store 162 enabling long-term storage of large data files. In addition, the server 160a, 160b and/or the clients 152 and 154 may be connected to a "cloud" computing service 156 enabling the remote storage of data, or even the remote computational information. In examples, the elements of the semantic network 30 are provided with security features that prevent any of the server 160a, 160b and/or the clients 152 and/or 154 from transferring private patient data to the remote cloud service 156.

In the example, the client tier 102 of a BioXM™ database previously discussed in FIG. 9 would be implemented on the first client 152 and, in examples the second client 154. The server tier 104 and the database tier 106 of the BioXM™ database would be implemented on the server 160a, 160b, although in examples the server tier 106 may be executed on or more other servers for reasons of load-balancing, for example. In examples, the load-balancing may be managed by the semantic network 30, for example via a "Hadoop" ™ cluster. It is to be noted that this description is simply one practical embodiment of the discussed technique. In other examples, the entire framework of client tier 102, server tier 104, and database tier 106 may be performed on the same computing device. In addition, the computing devices of the client tier 102 may, in examples, be "smart phones", or "tablet computing devices" for example.

Example Connectome Data

In the following tables, samples of the connectivity levels between nodes generated by the semantic network for different test subjects illustrated in FIGS. 13 to 20 are provided. Each row of the table comprises an indication of the relative connectivity between two stated brain structures (the origin brain structure and the target brain structure). For each figure, five samples of connections having a connection strength that has a strong negative deviation, a moderate negative deviation, and a low negative deviation compared to the expected (healthy) connection strength are shown. In other words, the following data is an example of comparing portions of a template connectivity graph with corresponding portions of a subject connectivity graph representation to provide an indication of a pathological condition of the subject.

The connectome information used as the basis for generating the figures of the present specification is based on measured connectome information publicly available and authorized for public use from "The Human Connectome Project", by Jesse A. Brown, Jeffrey D. Rudie, Anita Bandrowski, John D. Van Horn, Susan Y. Bookheimer, as discussed in the publication "The UCLA Multimodal Connectivity Database: A web-based platform for connectivity matrix sharing and complex network analysis" (2012), Frontiers in Neuroinformatics, 2012;6:28.doi: 10.3389/fninf.2012.00028.http://dx.doi.org/10.3389/fninf.2012.00028).

TABLE 2 sample of data generated in semantic network to generate FIG. 13.

| Origin Structure | Target Structure | Structural Connectivity | Negative Deviation |
|---|---|---|---|
| right frontal pole | right superior parietal lobule | 0 | −100 |
| left frontal pole | left postcentral | 0 | −100 |
| left frontal pole | left superior parietal lobule | 0.004902 | −99.8366 |
| right frontal pole | right postcentral | 0.004902 | −99.5098 |
| right superior frontal | right superior parietal lobule | 0.004902 | −99.5098 |
| ... | ... | ... | ... |
| right precentral | right supramarginal posterior | 9.29902 | −35.8688276 |
| left precentral | left paracingulate | 0.642157 | −35.7843 |
| left precentral | left paracingulate | 0.671569 | −32.8431 |
| left precentral | left supramarginal anterior | 214.80392 | −30.7084129 |
| left precentral | left postcentral | 2.764706 | −26.2745067 |
| ... | ... | ... | ... |
| left precentral | left angular | 162.47549 | 280.059626 |
| right frontal pole | right parietal operculum | 68.27451 | 290.140057 |
| left frontal pole | left superior parietal lobule | 19.926471 | 298.52942 |
| left precentral | left angular | 75.941176 | 321.895422 |
| left frontal orbital | left paracingulate | 19.436275 | 547.875833 |

TABLE 3 sample of data generated in semantic network to generate FIG. 14.

| Origin.Brain Structure | Target.Brain Structure | Patient Structural Connectivity | Negative Deviation |
|---|---|---|---|
| left temporal occipital fusiform | left lateral occipital superior | 0.068627 | −96.56865 |
| left lateral occipital superior | left temporal occipital fusiform | 0.068628 | −96.5686 |

TABLE 3-continued sample of data generated in semantic network to generate FIG. 14.

| Origin.Brain Structure | Target.Brain Structure | Patient Structural Connectivity | Negative Deviation |
|---|---|---|---|
| right lateral occipital superior | right temporal occipital fusiform | 0.102941 | −94.85295 |
| right temporal occipital fusiform | right lateral occipital superior | 0.102941 | −94.85295 |
| left occipital pole | left lateral occipital inferior | 0.406863 | −94.38809655 |
| . . . | . . . | . . . | . . . |
| right lingual | right lateral occipital superior | 254.7353 | 14.87498985 |
| left lateral occipital superior | left lateral occipital superior | 396.3529 | 14.88491014 |
| right lateral occipital superior | right lateral occipital superior | 236.7353 | 14.92004369 |
| right lateral occipital inferior | right occipital pole | 88.56863 | 15.02419481 |
| left lingual | left occipital pole | 234.6373 | 15.1593865 |
| . . . | . . . | . . . | . . . |
| left occipital pole | left temporal occipital fusiform | 49.57843 | 304.7218857 |
| left occipital pole | left temporal occipital fusiform | 61.86275 | 326.6396207 |
| right lingual | right occipital pole | 82.58333 | 346.3963784 |
| right lateral occipital superior | right lingual | 41.10294 | 356.6993444 |
| right occipital pole | right lingual | 100.5833 | 443.6936757 |

TABLE 4 sample of data generated in semantic network to generate FIG. 15.

| Origin.Brain Structure | Target.Brain Structure | Patient Structural Connectivity | Negative Deviation |
|---|---|---|---|
| left hippocampus | right cingulate anterior | 0.004902 | −99.8366 |
| right cingulate posterior | left hippocampus | 0.259804 | 95.66993333 |
| left hippocampus | right cingulate posterior | 0.259804 | 95.66993333 |
| left subcallosal | left cingulate posterior | 0.779412 | −90.25735 |
| right hippocampus | left cingulate anterior | 0.323529 | 90.04526154 |
| . . . | . . . | . . . | . . . |
| left cingulate anterior | right cingulate posterior | 230.9657 | 10.64224671 |
| right cingulate posterior | right cingulate anterior | 365.701 | 11.15531307 |
| left cingulate anterior | right cingulate anterior | 316.1863 | 12.7223779 |
| right cingulate anterior | right hippocampus | 11.89216 | 13.2586381 |
| right cingulate anterior | right cingulate posterior | 306.9069 | 13.35433426 |
| . . . | . . . | . . . | . . . |
| right hippocampus | right cingulate posterior | 23.10784 | 285.1307167 |

TABLE 4-continued sample of data generated in semantic network to generate FIG. 15.

| Origin.Brain Structure | Target.Brain Structure | Patient Structural Connectivity | Negative Deviation |
|---|---|---|---|
| right hippocampus | right cingulate posterior | 19.28922 | 285.78432 |
| right hippocampus | left cingulate posterior | 42.97549 | 290.6862727 |
| left parahippocampal posterior | right cingulate posterior | 104.3873 | 353.8576087 |
| right hippocampus | left parahippocampal posterior | 20.47059 | 411.7647 |

TABLE 5 sample of data generated in semantic network to generate FIG. 17.

| Origin.Brain Structure | Target.Brain Structure | Patient Structural Connectivity | Negative Deviation |
|---|---|---|---|
| right thalamus | right postcentral | 0.166667 | −94.44443333 |
| left thalamus | left precentral | 0.264706 | −93.38235 |
| left precentral | left postcentral | 10.71078 | −91.71312959 |
| left precentral | right precentral | 7.04902 | −83.01440964 |
| left thalamus | left postcentral | 2.764706 | −82.7205875 |
| . . . | . . . | . . . | . . . |
| left precentral | left postcentral | 152.78922 | −42.66821013 |
| left precentral | right precentral | 16.92647 | −41.63286207 |
| left thalamus | left precentral | 3.034314 | −39.31372 |
| right precentral | right postcentral | 229.11275 | −33.10576642 |
| right thalamus | right postcentral | 4.303922 | −31.137248 |
| . . . | . . . | . . . | . . . |
| left thalamus | left postcentral | 627.09314 | 1.635841167 |
| right thalamus | right precentral | 727.03431 | 8.189629464 |
| right precentral | right postcentral | 357.55392 | 11.91046009 |
| right thalamus | right precentral | 619.65196 | 15.39142644 |
| right precentral | right postcentral | 2.75 | 37.5 |

TABLE 6 sample of data generated in semantic network to generate FIG. 18.

| Origin.Brain Structure | Target.Brain Structure | Patient Structural Connectivity | Negative Deviation |
|---|---|---|---|
| right frontal orbital | right superior parietal lobule | 0 | −100 |
| right frontal orbital | right precuneous | 0 | −100 |
| left frontal pole | left postcentral | 0 | −100 |
| right superior frontal | right superior parietal lobule | 0.004902 | −99.5098 |
| right middle frontal | right postcentral | 0.02451 | −98.7745 |
| . . . | . . . | . . . | . . . |
| right frontal pole | right supramarginal posterior | 0.617647 | −69.11765 |
| right precentral | right superior parietal lobule | 5.098039 | −69.10279394 |
| right precentral | right superior parietal lobule | 39.56863 | −69.08700781 |
| right precentral | right postcentral | 8.13725 | −68.70288462 |
| right central opercular | right angular | 1.264706 | −68.38235 |
| . . . | . . . | . . . | . . . |
| right superior frontal | right parietal operculum | 1.808823 | 80.8823 |

TABLE 6-continued sample of data generated in semantic network to generate FIG. 18.

| Origin.Brain Structure | Target.Brain Structure | Patient Structural Connectivity | Negative Deviation |
|---|---|---|---|
| right frontal pole | right superior parietal lobule | 1.877451 | 87.7451 |
| left inferior frontal pars triangularis | left postcentral | 1.882353 | 88.2353 |
| left frontal pole | left postcentral | 1.995098 | 99.5098 |
| right frontal pole | right precuneous | 2.387255 | 138.7255 |

In the preceding specification, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

A computer program element comprises program code enabling a computer to carry out the computer-implemented method described herein. A computer program may be stored and distributed on a suitable medium, such as a solid-state medium, and optical storage medium, and/or supplied with or as part of other hardware. A computer program may also be distributed via the Internet or other wired or wireless telecom dictation systems. A computer program product comprises a computer program element.

The term "communication network" as used herein encompasses any type of wireless network, such as a WIFI, GSM, UMTS or other wireless digital network or a cable based network, such as Ethernet or the like. In particular, the communication network can implement the Internet protocol (IP). For example, the communication network comprises a combination of cable-based and wireless networks. The semantic network discussed in the present disclosure can be provided on a server or computer and configured to communicate with a hospital PACS system and/or with a medical scanner having appropriate communication capabilities through a communication network.

Reference throughout the preceding specification to "one embodiment", "an embodiment", "one example" or "an example", "one aspect" or "an aspect" means that a particular feature, structure or characteristic described in connection with the embodiment or example is included in at least one embodiment of the present invention. Thus, appearances of the phrases "in one embodiment", "in an embodiment", "one example" or "an example", "one aspect" or "an aspect" in various places throughout this specification are not necessarily all referring to the same embodiment or example.

In this specification, the term "comprising" does not exclude other elements or steps. The word "a" or "an" does not exclude a plurality. The phrase "and/or" used in this specification should be understood to mean a "either or both" of the elements joined. If multiple elements are listed in an "and/or" statements, they should be construed in the same way - in other words "one or more" of the joint elements. Other elements may be present other than those specifically defined in such an "and/or" clause. The term "or" should be interpreted to have the same meaning as "and/or".

In this specification, unless indicated to the contrary, in methods comprising more than one step, the order of the steps of the method is not necessarily limited.

Furthermore, the particular features, structures, or characteristics may be combined in any suitable combinations and/or sub-combinations in one or more embodiments or examples.

The invention claimed is:

1. A computer-implemented method for computing a pathological condition of a subject, said method comprising:
    a) obtaining (10) initial cranial image data of a subject from an input interface, and incorporating the initial cranial image data into a knowledge model comprised within a semantic network stored in a memory;
    b) performing (12), via a processor, at least one processing sequence on the initial cranial image data using the semantic network to thus provide, in the semantic network, at least one element comprising topographical data of the subject's brain, or a portion of the subject's brain, referenced to a reference coordinate system; wherein the at least one processing sequence performs at least one state iteration of at least a portion of the semantic network from a first state into a second state;
    c) comparing (14) the topographical data of the subject's brain to one, or more pathological condition prediction elements of the semantic network to form an indication of a pathological condition of the subject; and
    d) generating (16) an additional element in the semantic network comprising the indication of the pathological condition of the subject,
    wherein said method further comprises:
    generating a subject connectivity graph element of the least one topographical data in the semantic network, wherein the subject connectivity graph element comprises a subject connectivity graph representation of nodes and interconnections between nodes based on functional and/or structural connections between a portion of the subject's brain,
    obtaining at least one template connectivity graph element representing a pathological condition, wherein the template connectivity graph element comprises an idealized, averaged, control, or measured template connectivity graph indicative of a brain, or portion of a brain wherein the template connectivity graph is indicative of a neurological condition;
    comparing, within the semantic network, portions of the template connectivity graph with corresponding portions of the subject connectivity graph representation;
    identifying similarities of the template connectivity graph and the corresponding portions of the subject connectivity graph representation; and
    providing the indication of a pathological condition of the subject if the similarities of the template connectivity graph and the corresponding portions of the subject connectivity graph exceed a threshold.

2. The computer-implemented method according to claim 1, further comprising: calculating a subject connectivity statistic of the nodes of the subject connectivity graph element; and providing the indication of the pathological condition of the subject by comparing the subject connectivity statistic to a pathological condition prediction statistic.

3. The computer-implemented method according to claim 2, wherein the subject connectivity statistic is at least one of associativity, density, modularity, mean of the shortest paths, efficiency, transitivity, weighted characteristic path length, weighted clustering coefficient, small-world parameter, betweenness centrality, or local efficiency of the subject connectivity graph, or a portion of the subject connectivity graph.

4. The computer-implemented method according to claim 1, wherein the subject connectivity statistic or template connectivity graph characterizes multiple sclerosis or Alzheimer's disease.

5. The computer-implemented method according to claim 1, further comprising: annotating the topographical data with a brain atlas defining brain regions registered to the topographical data in the reference coordinate system; enlarging a formal grammar of the semantic network based on the brain regions defined in the brain atlas; and generating the additional element in the semantic network comprising the indication of the pathological condition of the subject based on a selection of at least one brain region in the brain atlas.

6. The computer-implemented method according to claim 1, further comprising: annotating the topographical data with a functional or anatomical ontology of brain structures defining functional or anatomical properties of brain regions registered to the topographical data in the reference coordinate system; enlarging a formal grammar of the semantic network based on the functional or anatomical ontology of brain regions; and generating the additional element in the semantic network comprising the indication of the pathological condition of the subject based on a selection of at least one brain structure in the functional or anatomical ontology.

7. The computer-implemented method according to claim 6, further comprising: selecting a subset of the topographical data of the subject's brain based on the symptom data, and optionally a brain atlas comprised in the semantic network, and forming the indication of the pathological condition of the subject based on the subset of the topographical data or the symptom data.

8. The computer-implemented method according to claim 1, further comprising: obtaining symptom data or input classification data of the subject from the input interface, and incorporating the symptom data into the knowledge model comprised within a semantic network stored in the memory; forming the indication of the pathological condition of the subject in the semantic network using the symptom data and the at least one element comprising topographical data.

9. The computer-implemented method according to claim 1, wherein the initial cranial image data of the subject comprises a first time index defining an acquisition time of the initial cranial image data; and further comprising: obtaining subsequent cranial image data of the subject from the input interface at a second time index and incorporating the subsequent cranial image data into the knowledge model comprised within the semantic network stored in the memory and performing steps b), c), and d) on the subsequent cranial image data using the semantic network to thus generate a further additional element in the semantic network comprising a further indication of the pathological condition of the subject at the second time index; and comparing the additional element and the further additional element in the semantic network to identify a change in the pathological condition in-between the first time index and the second time index.

10. The computer-implemented method according to claim 1, further comprising: accessing, via or in the semantic network, a neurological simulation element, wherein the neurological simulation element is configured obtain the at least one element comprising topographical data as a starting point of a neurological simulation; generating a simulated topographical data element in the semantic network as an output of the neurological simulation element applied to the topographical data.

11. The computer-implemented method according to claim 1, further comprising: outputting the indication of the pathological condition of the subject based on the additional element in the semantic network.

12. The computer-implemented method according to claim 1, further comprising: receiving a user query; generating a request by transforming the user query into the formal linguistic specification defined by the semantic network; and obtaining an output report to display the indication of the pathological condition of the subject using the additional element in the semantic network based on the user query.

13. The computer-implemented method according to claim 1, wherein the initial cranial image data comprises structural MRI data, and the at least one processing sequence comprises a structural MRI data processing workflow or wherein the initial cranial image data comprises MRI data, and the at least one processing sequence comprises a functional MRI data processing workflow; and/or wherein the initial cranial image data comprises PET data, and the at least one processing sequence comprises a PET data processing workflow; or wherein the initial cranial image data comprises DTI data, and the at least one processing sequence comprises a DTI data processing workflow; or wherein the initial cranial image data comprises MEG data, and the at least one processing sequence comprises a MEG data processing workflow.

14. A non-transitory computer program element comprising instructions that, when executed by a processor of a computer, enable the processor of the computer to carry out the computer-implemented method of claim 1.

15. A non-transitory computer program product, tangibly embodied on a non-transitory, carrier medium, said non-transitory computer program product comprising the non-transitory computer program element of claim 14.

16. An apparatus (20) for computing a pathological condition of a subject, said apparatus comprising: an input interface (22); a a processor (24); a memory (26); and an output interface (28);
  wherein the input interface is configured to obtain initial cranial image data of a subject from the input interface (22) and to incorporate the initial cranial image data into a knowledge model comprised within a semantic network stored in the memory (26);
  wherein the processor (24) is configured to perform at least one processing sequence on the initial cranial image data using the semantic network to thus provide, in the semantic network stored in the memory, at least one element comprising topographical data of the subject's brain, or a portion of the subject's brain, referenced to a reference coordinate system;
  wherein the processor (24) is configured to perform the at least one processing sequence comprising at least one state iteration of at least a portion of the semantic network in the memory from a first state into a second state;
  wherein the processor (24) is configured to compare the topographical data of the subject's brain to one, or more pathological condition prediction elements of the semantic network in the memory to form an indication of a pathological condition of the subject;

wherein the processor (24) is configured to generate an additional element in the semantic network comprising the indication of the pathological condition of the subject;

wherein the processor is further configured to carry out steps of: generating a subject connectivity graph element of the least one topographical data in the semantic network, wherein the subject connectivity graph element comprises a subject connectivity graph representation of nodes and interconnections between nodes based on functional or structural connections between a portion of the subject's brain, said method further comprising obtaining at least one template connectivity graph element representing a pathological condition, wherein the template connectivity graph element comprises an idealized, averaged, control, or measured template connectivity graph indicative of a brain, or portion of a brain wherein the template connectivity graph is indicative of a neurological condition; comparing, within the semantic network portions of the template connectivity graph with corresponding portions of the subject connectivity graph representation; identifying similarities of the template connectivity graph and the corresponding portions of the subject connectivity graph representation; providing the indication of a pathological condition of the subject if the similarities of the template connectivity graph and the corresponding portions of the subject connectivity graph exceed a threshold.

17. A system for computing a neurological condition of a subject, comprising: a medical image acquisition apparatus; and an apparatus according to claim 16; wherein the medical image acquisition apparatus is one or more of an MRI scanner, a CT scanner, a PET scanner, or a MEG scanner.

18. A method for diagnosing a subject with a pathological condition, said method comprising:

obtaining one or more sets of initial cranial image data of a subject using one or more items of medical image acquisition equipment;

providing the initial cranial image data of a subject to an input interface of an apparatus according to claim 16; and receiving from the output interface of the apparatus according to claim 16, a report comprising output classification data of the subject.

* * * * *